United States Patent
Gupta

(10) Patent No.: US 7,572,933 B2
(45) Date of Patent: Aug. 11, 2009

(54) SKIN AND HAIR RESTORATION BY NATURAL AMINO ACID PEPTIDE COMPLEXES

(75) Inventor: Shyam K Gupta, Scottsdale, AZ (US)

(73) Assignee: Bioderm Research, Scottsdale, AZ (US)

( * ) Notice: Subject to any disclaimer, the term of this patent is extended or adjusted under 35 U.S.C. 154(b) by 0 days.

(21) Appl. No.: 12/182,864

(22) Filed: Jul. 30, 2008

(65) Prior Publication Data

US 2008/0287536 A1 Nov. 20, 2008

Related U.S. Application Data

(63) Continuation-in-part of application No. 11/309,437, filed on Aug. 4, 2006, now Pat. No. 7,427,690.

(51) Int. Cl.
*C07C 249/00* (2006.01)
*C07C 251/24* (2006.01)

(52) U.S. Cl. .................. 562/433; 562/440
(58) Field of Classification Search .................. None
See application file for complete search history.

(56) References Cited

OTHER PUBLICATIONS

Sheehan et al. Journal of the American Chemical Soc. 1962, v84, p. 2417.*

* cited by examiner

Primary Examiner—Daniel M Sullivan
Assistant Examiner—Yevegeny Valenrod

(57) ABSTRACT

This invention relates to certain skin and hair care agents of formula (I), derived from natural amino acids and peptides. These agents provide multi-functional treatment of enzyme-related topical problems, for example, darkened skin including age spots, circles around eyes and stretch marks; skin conditions related to acne including excess facial oil and facial pore size; premature hair aging including hair loss and graying; inflammation including intra-cellular and extra-cellular inflammation; skin aging including wrinkles and fine lines; loss of collagen including thinning skin and loss of skin pliability; malfunction of tyrosinase group of enzymes; malfunction of matrix metalloprotease group of enzymes; and combinations thereof:

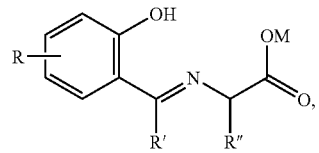

Formula (I)

Wherein,
R, R', and R"=any substituent(s); and
M=H, Li, Na, K, Ca, Mg, Zn, Mn, Cu, Fe, Co, Mo, V, Cr, Ammonium, Alkyl ammonium, and Nitrogen Heterocyclic ammonium.

6 Claims, 18 Drawing Sheets

Chemical Name: 2-{[1-(2-Hydroxyaryl)alkylidene]amino}alkanoic acid

| R | R' | R" |
|---|---|---|
| Hydroxy | Alkyl | Alkyl |
| Alkyl | Substituted Alkyl | Substituted Alkyl |
| Substituted Alkyl | Heterocyclic | Aryl |
| Halogen | | Heterocyclic |
| Oxyalkyl | | |
| Oxyaryl | | |

N-[(Hydroxyaryl)alkylidene]Amino Acid

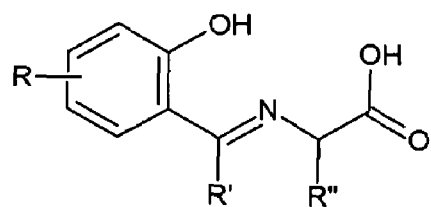
Chemical Name: 2-{[1-(2-Hydroxyaryl)alkylidene]amino}alkanoic acid
| R | R' | R" |
|---|----|----|
| Hydroxy | Alkyl | Alkyl |
| Alkyl | Substituted Alkyl | Substituted Alkyl |
| Substituted Alkyl | Heterocyclic | Aryl |
| Halogen | | Heterocyclic |
| Oxyalkyl | | |
| Oxyaryl | | |
Figure 1. N-[(Hydroxyaryl)alkylidene]Amino Acid

Structure A

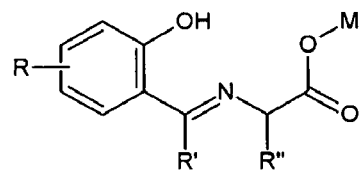

M = Monovalent Atoms, Metals, or Ions [H, Li, Na, K, Ammonium, Various Alkylammonium, and Salts of Nitrogen Heterocyclics]

Structure B

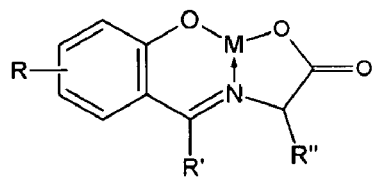

({[2-(hydroxy-κO)alkylidene]amino-κN}acetato-kO)Metal

M = Divalent Metals

Structure C

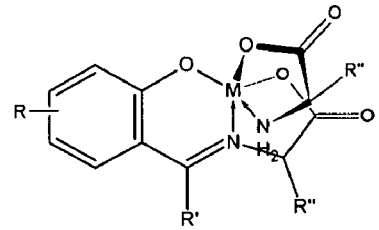

M = Polyvalent Metals

Divalent and Polyvalent Metals, M = Ti, V, Cr, Mn, Fe, Co, Ni, Cu, Zn, Se, Mo

R, R', R" = as in Figure 1

Figure 2. N-[(Hydroxyaryl)alkylidene]Amino Acids and Their Metal Complexes

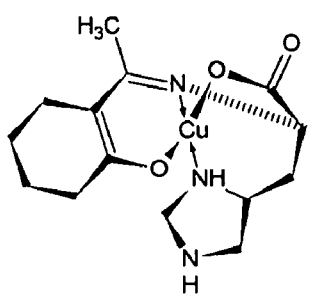 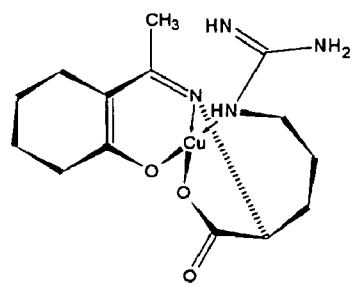
N-[(2-Hydroxyphenyl)ethylidene] Histidine Cu    N-[(2-Hydroxyphenyl)ethylidene] Arginine Cu
Figure 3. N-[(Hydroxyaryl)alkylidene] Amino Acid Copper "Crown Complexes"

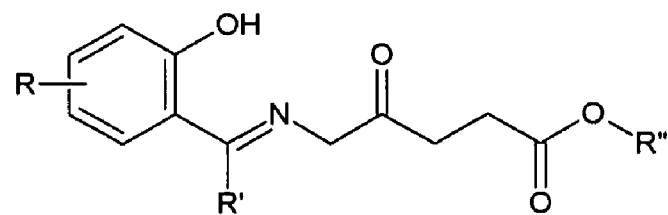
Chemical Name: 2-{[1-(2-Hydroxyaryl)alkylidene]amino}levulinic acid
| R | R' | R" |
|---|----|----|
| Hydroxy | Alkyl | H |
| Alkyl | Substituted Alkyl | Na |
| Substituted Alkyl | Heterocyclic | |
| Halogen | | |
| Oxyalkyl | | |
| Oxyaryl | | |
Figure 4. N-[(Hydroxyaryl)alkylidene]Levulinic Acid

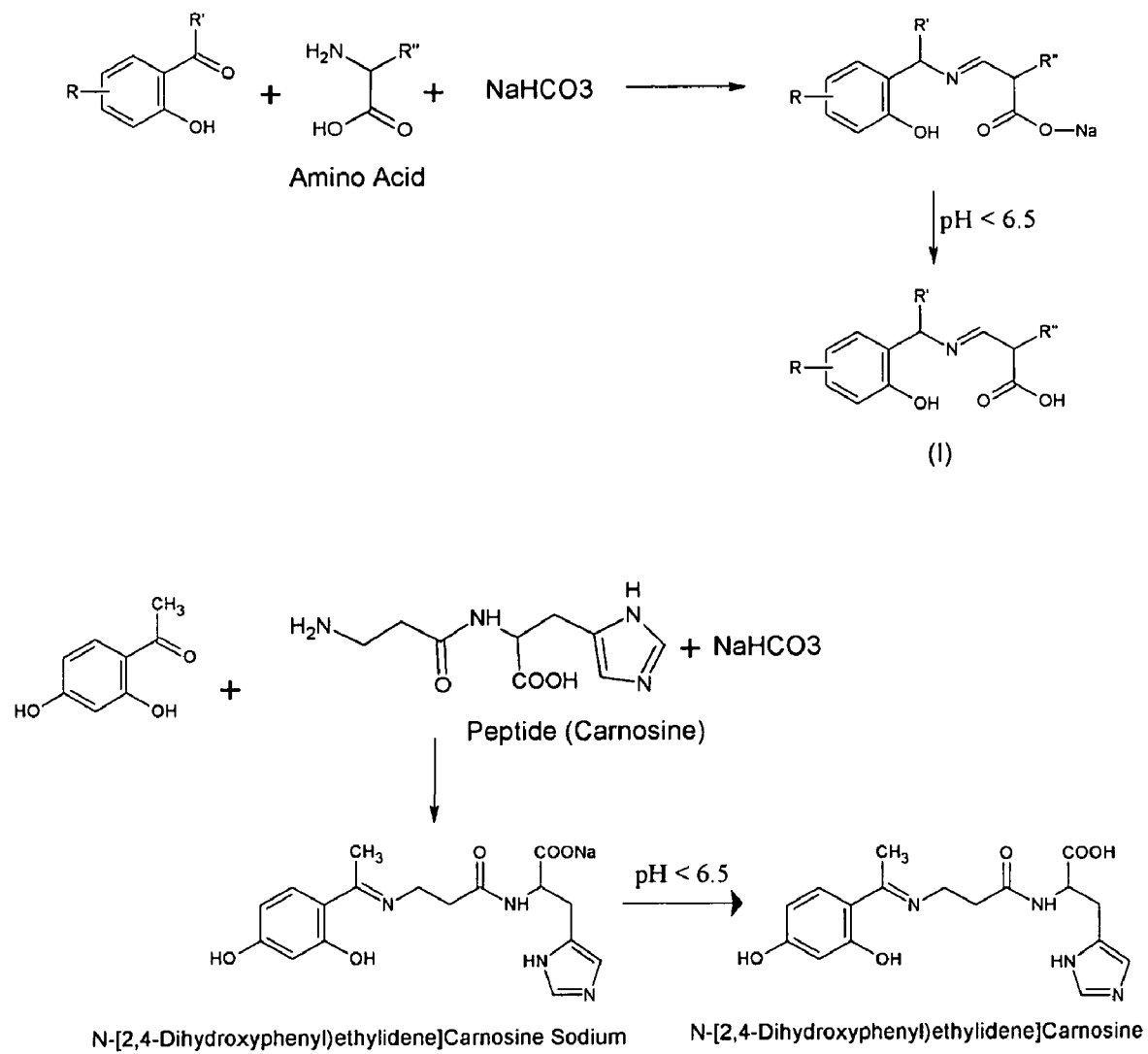
Figure 5. Example of the Preparation of N-[(Hydroxyaryl)alkylidene]Amino Acids and N-[(Hydroxyaryl)alkylidene]Peptides

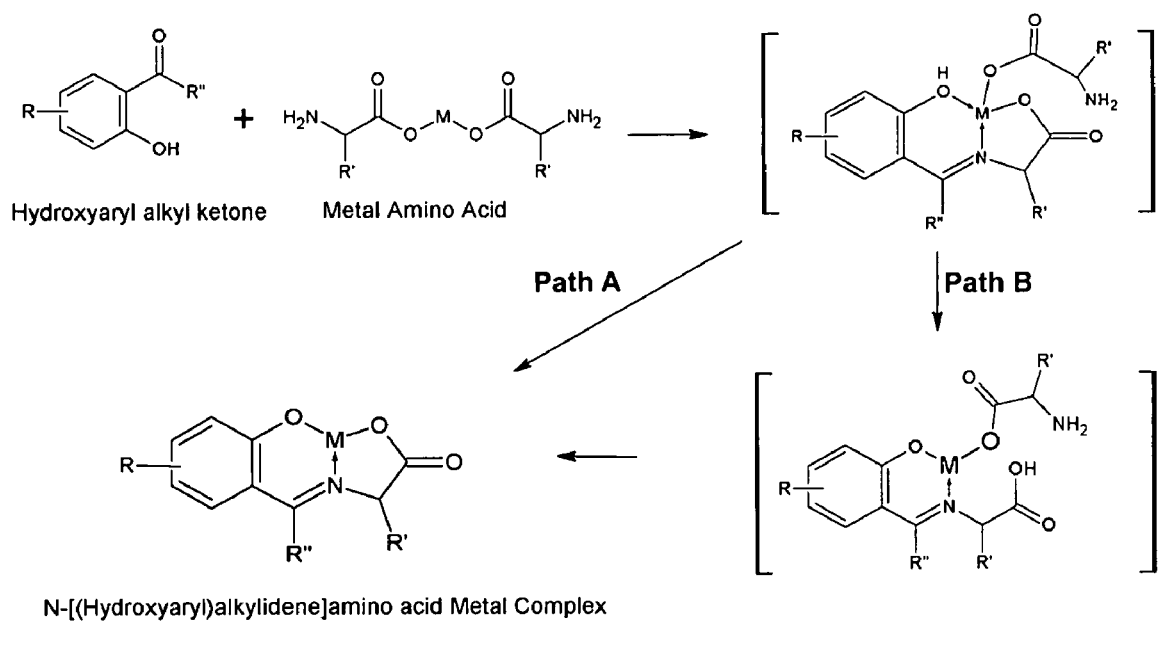
Figure 6. Preparation of N-[(Hydroxyaryl)alkylidene] Amino Acid Metal Complexes

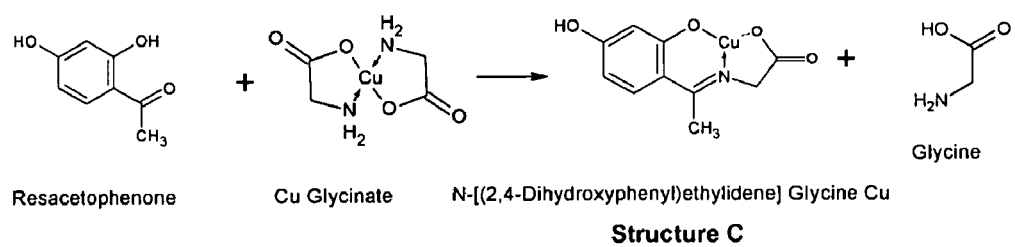
Resacetophenone    Cu Glycinate    N-[(2,4-Dihydroxyphenyl)ethylidene] Glycine Cu    Glycine
Structure C
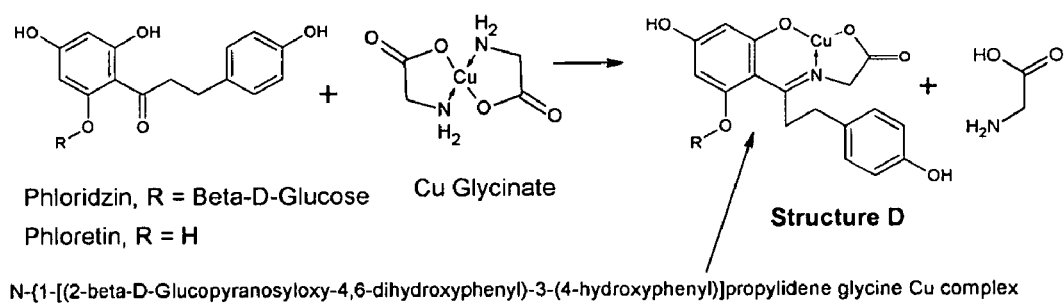
Phloridzin, R = Beta-D-Glucose    Cu Glycinate
Phloretin, R = H
Structure D
N-{1-[(2-beta-D-Glucopyranosyloxy-4,6-dihydroxyphenyl)-3-(4-hydroxyphenyl)]propylidene glycine Cu complex
Figure 7. Preparation of N-[(Hydroxyphenyl)alkylidene] Glycine Copper Complex Route A
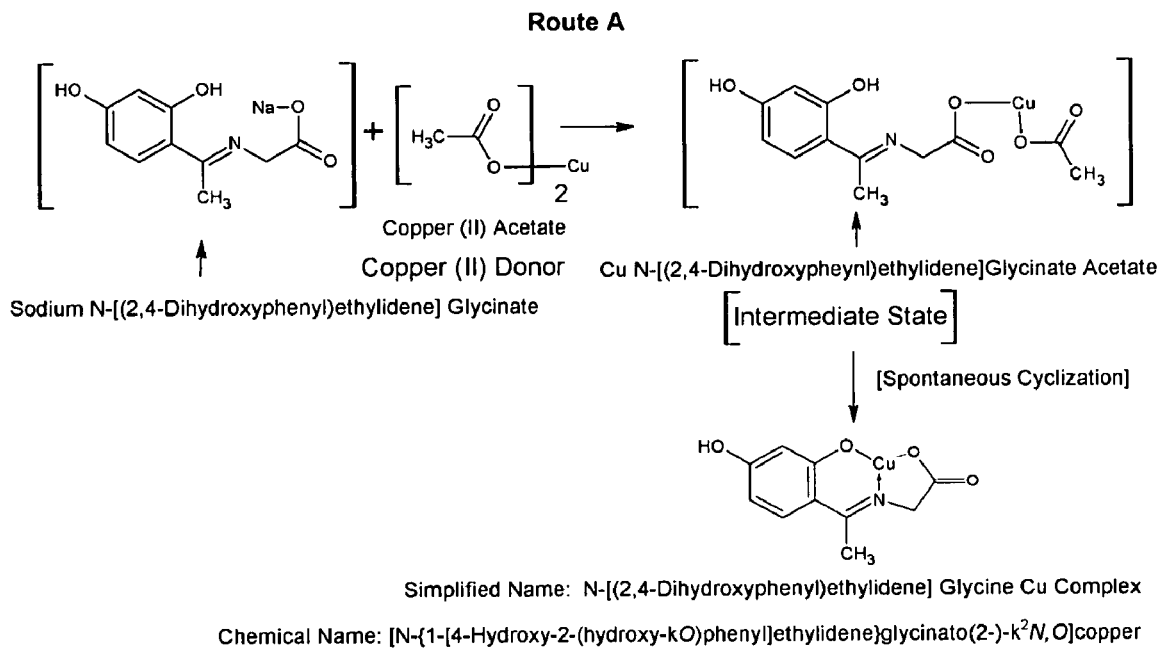
Simplified Name: N-[(2,4-Dihydroxyphenyl)ethylidene] Glycine Cu Complex
Chemical Name: [N-{1-[4-Hydroxy-2-(hydroxy-kO)phenyl]ethylidene}glycinato(2-)-k$^2$N,O]copper
Route B
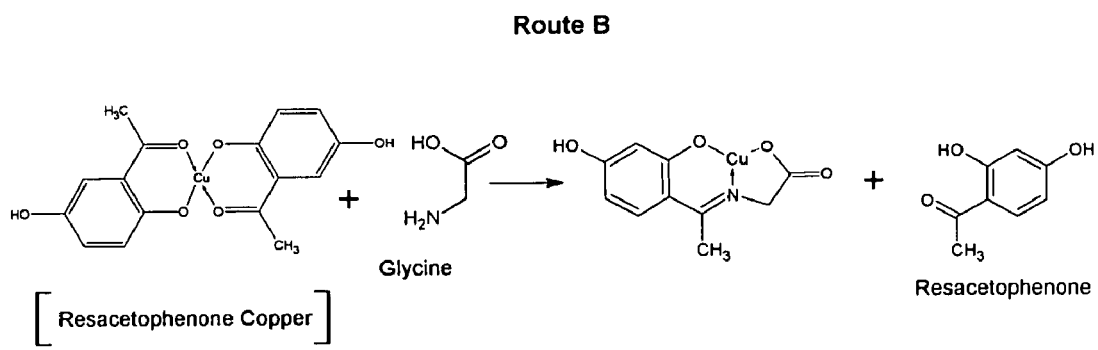
Figure 8. Alternate Preparation of N-[(Hydroxyaryl)ethylidene] Amino Acid Metal Complex

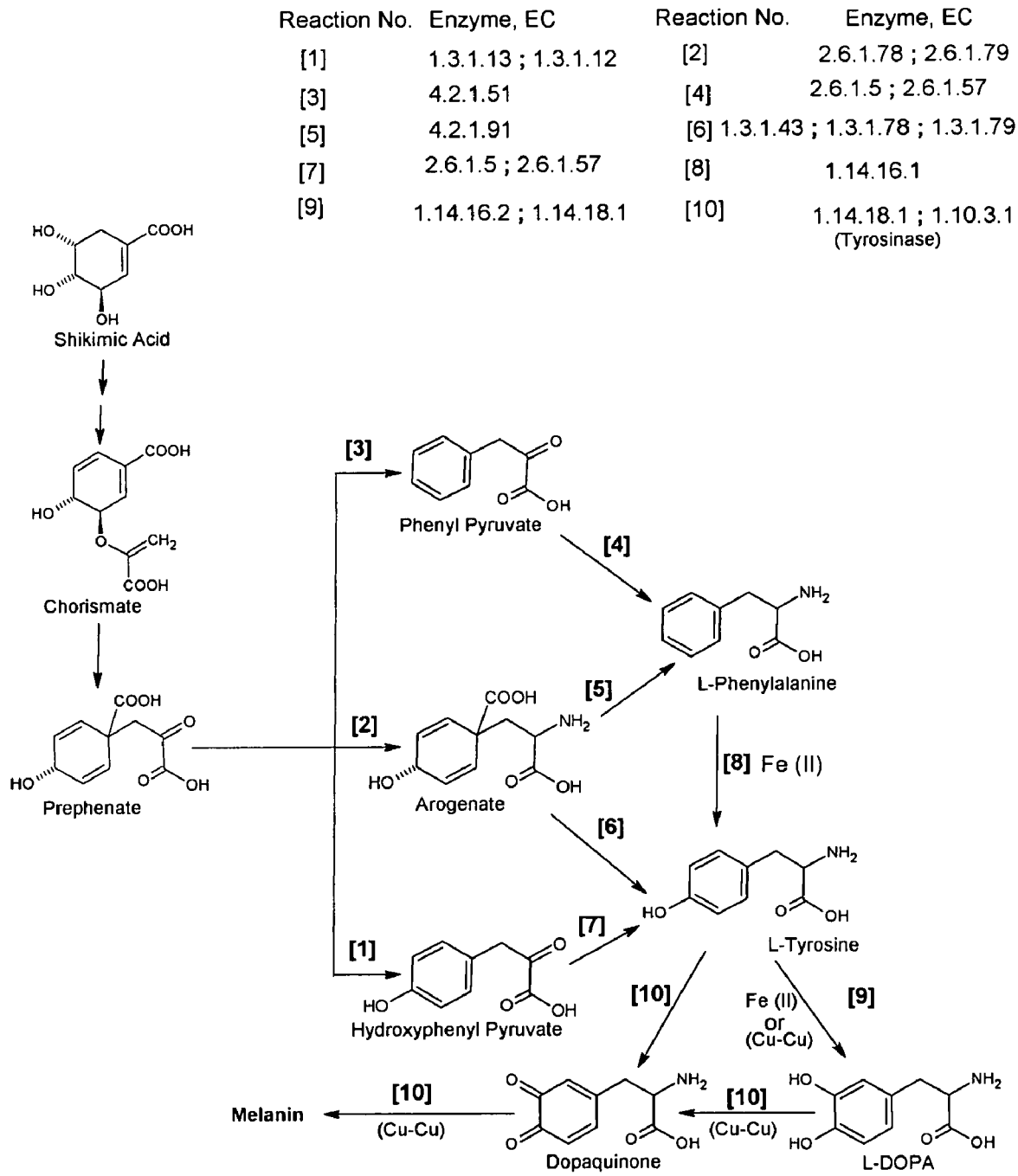
Figure 9. L-Tyrosine & Melanin Biosynthesis via Shikimate Pathway

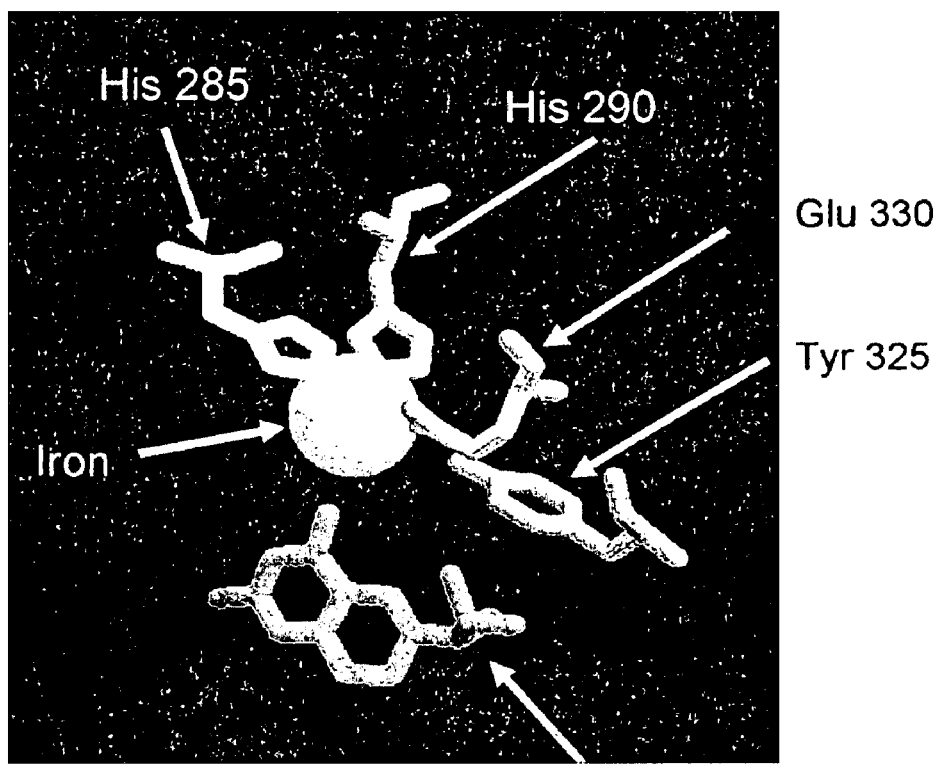
Figure 10. Active Site of Phenylalanine Hydroxylase

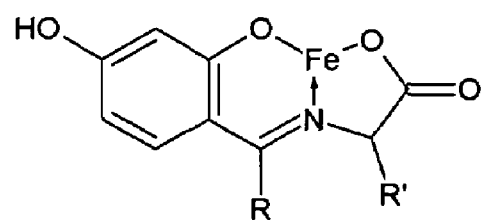
Figure 11. Iron Chelate of N-[(Hydroxyaryl)Alkylidene]Amino Acid

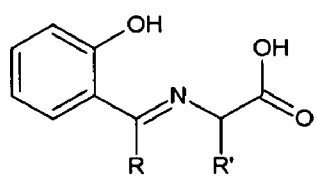 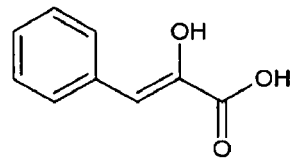
Structure E                              Structure F
Figure 12. Structural Similarity of N-[(Hydroxyaryl)Alkylidene] Amino Acids (Structure E) and Enolic Form of Phenyl Pyruvate (Structure F)

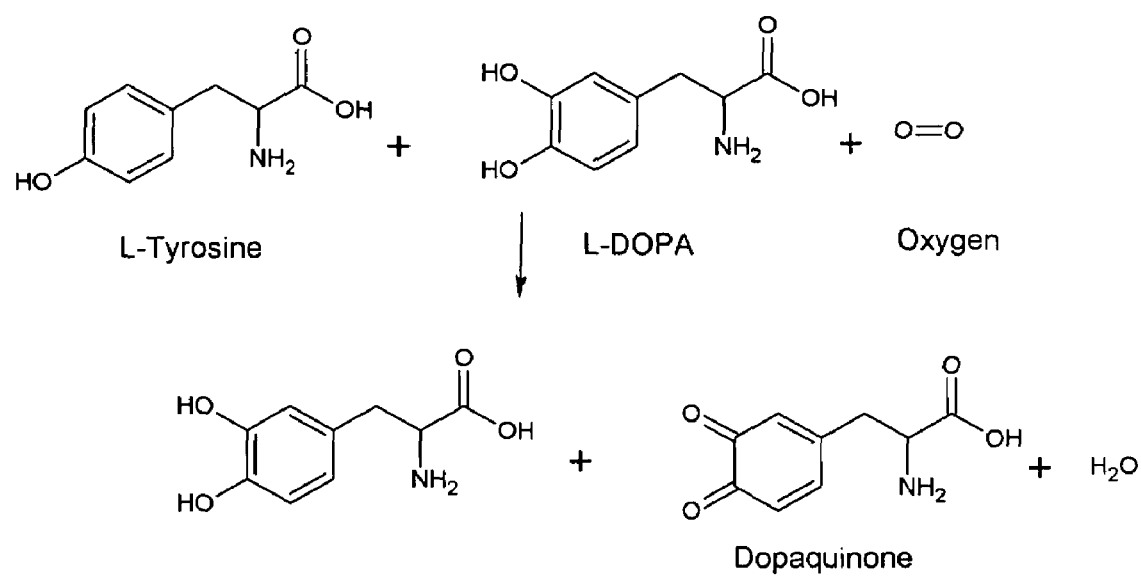
Figure 13. Reaction Catalyzed by Monophenol Monooxigenase [EC 1.14.18.1]

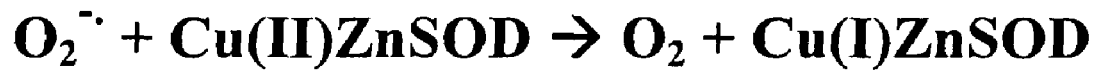
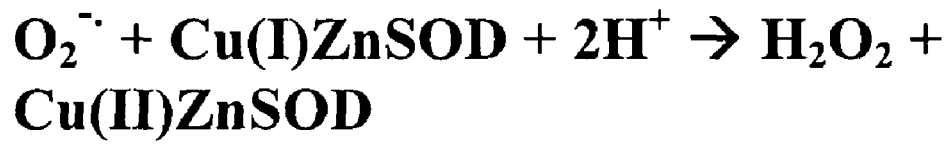
Figure 14. Dismutation of Superoxide Anion Radical by SOD

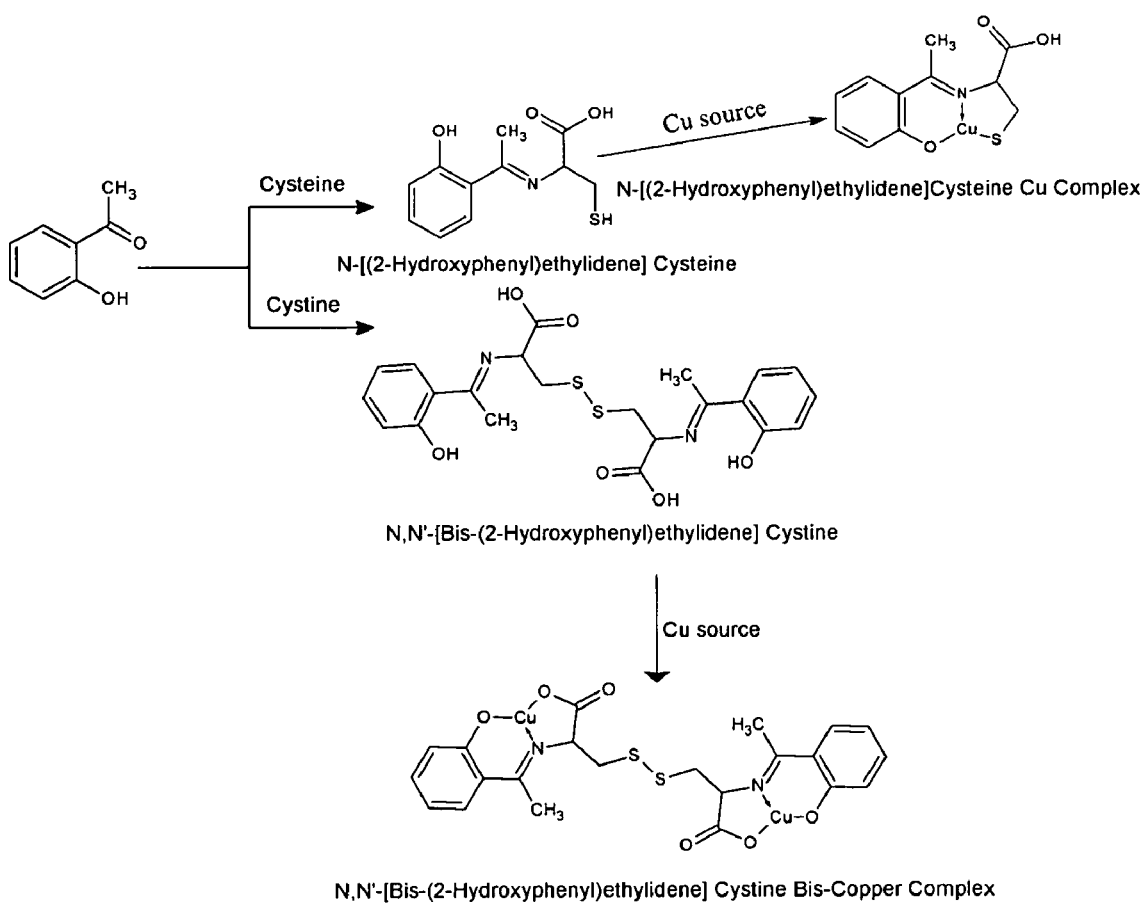
Figure 15. Cystine & Cysteine Schiff's Bases and Their Cu Complexes

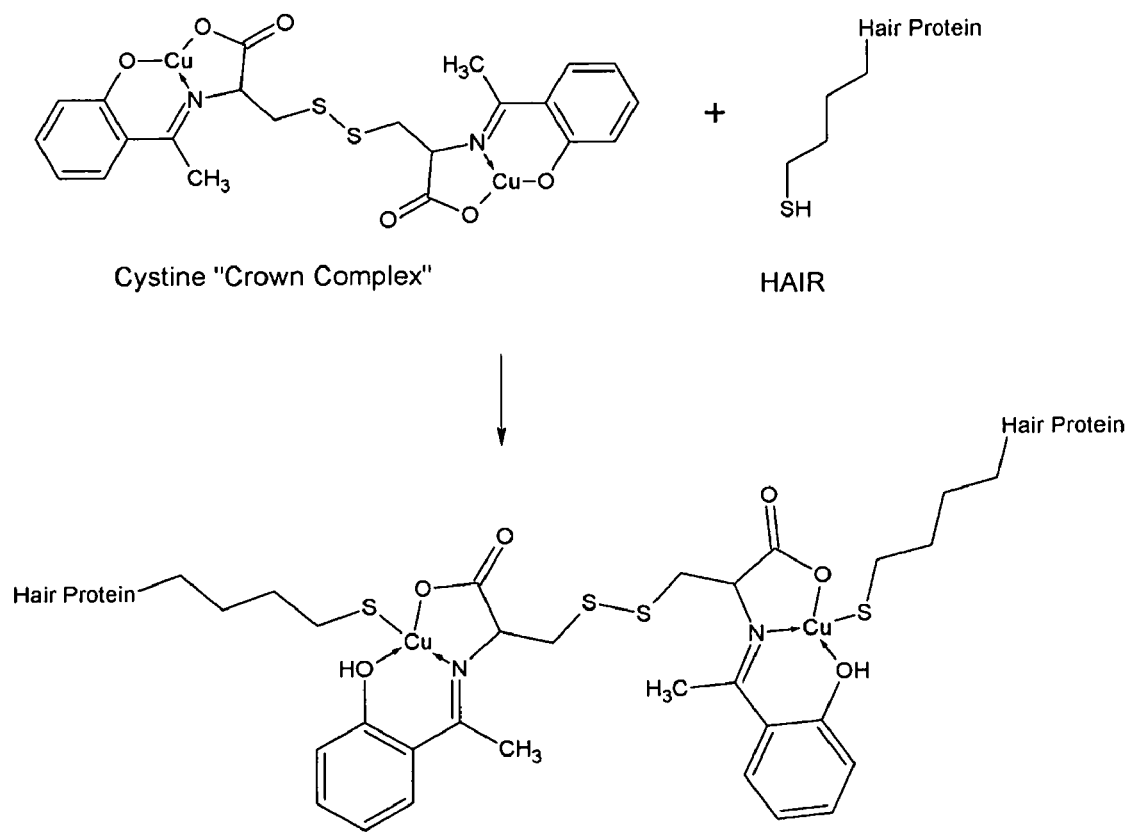
Figure 16. Binding of "Cystine Crown Complex" with -SH Groups of Cysteine in Hair

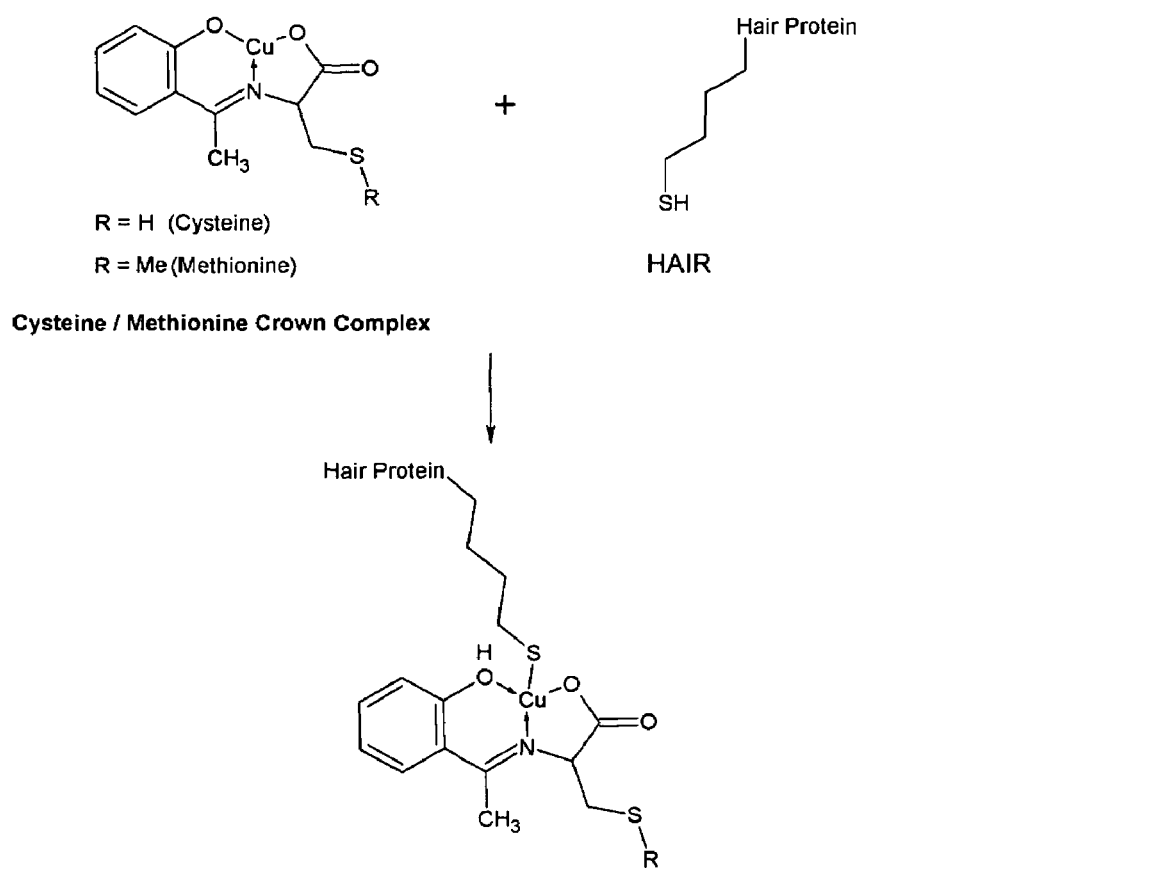
Figure 17. Binding of Cysteine / Methionine Crown Complex with -SH Groups of Cysteine in Hair

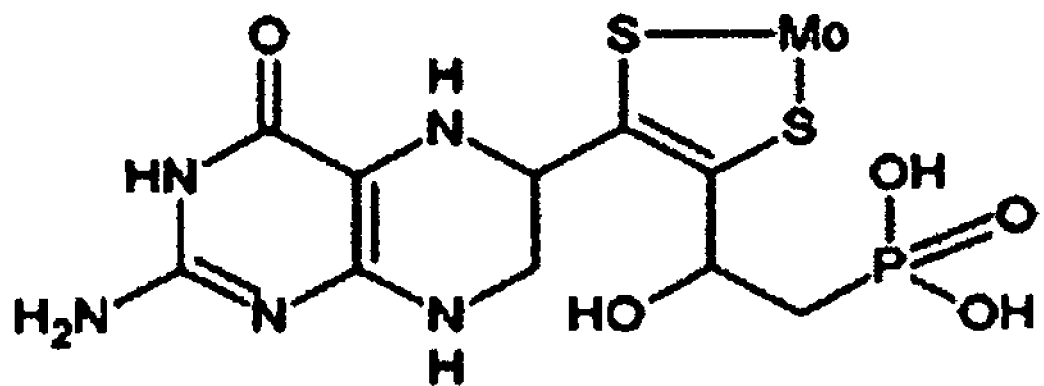
Figure 18. Molybdopterin

US 7,572,933 B2

SKIN AND HAIR RESTORATION BY NATURAL AMINO ACID PEPTIDE COMPLEXES

BACKGROUND OF THE INVENTION

This invention is a continuation-in-part of U.S. patent application Ser. No. 11/309,437 (filed Aug. 4, 2006), which was published as U.S. patent application pre-grant publication 20070099886. The present invention discloses topical treatment for skin and hair restoration by the compositions of the above invention.

This invention relates to certain N-[(Hydroxyaryl)alkylidene]amino acids, also known as "Amino Acid Schiff's Bases", which are derived from Hydroxyaryl alkyl ketones and amino acids or peptides, and metal salts or complexes thereof. These are beneficial for the treatment of skin and hair disorder or condition via up-regulation (activation) or down-regulation (inhibition) of enzyme mechanisms related in common to said disorder(s) or condition(s). The method of present treatment is thus applicable to a group of disorders or conditions that are common to said enzymes, thus providing multiple treatment benefits via the application of a single composition. This multi-function treatment method of topical disorders or conditions is thus novel in itself.

In a surprising and unexpected discovery, the N-[(Hydroxyaryl)alkylidene]amino acids and their trace metal complexes of the present invention are useful for topical application for the inhibition or activation of metal-activated enzymes and metalloenzymes, such as tyrosinase group, which includes Phenylalanine Hydroxylase, Tyrosine Transaminase, Phenylalanine Transaminase, and DOPA oxidase; various MMP (Matrix metalloproteases), Superoxide dismutase (SOD), which includes SOD-1, SOD-2, and SOD03; 5-Alpha Reductase, and citrate lyase.

A method of topical application is also disclosed, which provides a treatment of groups of inter-related enzyme dysfunction that cause said skin or hair condition such as darkened skin including age spots, circles around eyes and stretch marks; skin conditions related to acne including excess facial oil and facial pore size; premature hair aging including hair loss and graying; inflammation including intra-cellular and extra-cellular inflammation; skin aging including wrinkles and fine lines; loss of collagen including thinning skin and loss of skin pliability; malfunction of tyrosinase group of enzymes; malfunction of matrix metalloprotease group of enzymes; and combinations thereof. The present method thus provides multiple treatments that are enzymatically related, for example treatment of darkened skin including age spots, circles around the eyes and stretch marks, all of which are caused by malfunctioning of tyrosinase group of enzymes. Similarly, treatment of loss of collagen including thinning skin and loss of skin pliability is possible, as malfunctioning of matrix metalloprotease group of enzymes causes all of which. The treatment of premature hair aging including premature hair loss and hair graying via a single treatment is possible, as malfunctioning of tyrosinase group of enzymes and matrix metalloprotease group of enzymes is the common cause for all of which.

BRIEF DESCRIPTION OF THE DRAWINGS

[FIG. 1]. [(Hydroxyaryl)alkylidene]Amino Acid.
[FIG. 2]. [(Hydroxyaryl)alkylidene]Amino Acids and their Metal Complexes.
[FIG. 3]. [(Hydroxyaryl)alkylidene]Amino Acid Cu "Crown Complexes".
[FIG. 4]. N-[(Hydroxyaryl)alkylidene] levulinic acid.
[FIG. 5]. Example of the Preparation of N-[(Hydroxyaryl)alkylidene]Amino Acids and N-[(Hydroxyaryl)alkylidene] Peptides.
[FIG. 6]. Preparation of N-[(Hydroxyaryl)alkylidene] Amino Acid Metal Complexes.
[FIG. 7]. Preparation of N-[(2,4-Dihydroxyphenyl)alkylidene]Glycine Cu Complex.
[FIG. 8]. Alternate Preparation of N-[(Hydroxyaryl)alkylidene]Amino Acid Metal Complex.
[FIG. 9]. L-Tyrosine and Melanin Biosynthesis via Shikimate Pathway.
[FIG. 10]. Active-Site of Phenylalanine Hydroxylase.
[FIG. 11]. Iron Chelate of N-[(Hydroxyaryl)alkylidene] Amino Acid.
[FIG. 12]. Structural Similarity of N-[(Hydroxyaryl)alkylidene]Amino Acids (A) and Enolic Form of Phenyl Pyruvate (B).
[FIG. 13]. Reaction Catalyzed by Monophenol Monooxigenase.
[FIG. 14]. Dismutation of Superoxide Anion by SOD.
[FIG. 15]. Cystine & Cysteine Schiff's Bases and their Cu Complexes.
[FIG. 16]. Binding of "Cystine Crown Complex" with —SH Groups of Cysteine in Hair.
[FIG. 17]. Binding of Cysteine & Methionine "Crown Complex" with —SH Groups of Cysteine in Hair.
[FIG. 18]. Molybdopterin.

DETAILED DESCRIPTION

This invention relates to certain N-[(Hydroxyaryl)alkylidene]amino acids, also known as "Amino Acid Schiff's Bases", mostly in their optically active forms, and having general chemical structure in FIG. 1. These are derived from Hydroxyaryl alkyl ketones and amino acids or peptides. These are beneficial for multifunction topical application for treatment of skin and hair disorder or condition.

This invention also relates to certain metal complexes of Schiff's bases from natural amino acids and peptides, for example N-[(Hydroxyaryl)alkylidene]amino acids derived from alpha-amino acids, having general chemical structure in FIG. 2. The complexes that contain a monovalent metal, atom, or group; such as H, Li, Na, K, and various ammonium, alkyl ammonium, and nitrogen heterocyclics; are in open chain form (Structure A, FIG. 2). The complexes that contain a divalent or a polyvalent metal (Structure B, FIG. 2), surprisingly and unexpectedly, have a cyclic crown-like appearance in their three-dimensional optically active chemical structure in which ortho-hydroxyl group of the aryl moiety binds with the metal atom via electron transfer, for example N-[(Hydroxyaryl)alkylidene]histidine copper "Crown Complex" and N-[(Hydroxyaryl)alkylidene]arginine copper "Crown Complex", the proposed structure of both shown in FIG. 3.

[FIG. 1].
[FIG. 2].
[FIG. 3].

The other amino acids, such as beta amino acids, gamma-amino acids, and delta-amino acids, also form corresponding N-[(Hydroxyaryl)alkylidene]amino acids. For example, the reaction of levulinic acid, or its sodium salt, provides N-[(Hydroxyaryl)alkylidene]levulinic acid, or the corresponding sodium salt, as shown in [FIG. 4].

[FIG. 4].

In a surprising and unexpected discovery, the N-[(Hydroxyaryl)alkylidene]amino acids of the present invention and their trace metal complexes are useful for topical application, including the activation or inhibition of metal-activated enzymes and metalloenzymes, such as Phenylalanine Hydroxylase, Tyrosine Transaminase, Phenylalanine Transaminase, Tyrosinases, various MMP (Matrix metalloproteases), Superoxide dismutases, 5-Alpha Reductase, and citrate lyase.

The N-[(Hydroxyaryl)alkylidene]amino acids and their trace metal complexes disclosed in the present invention provide multifunction treatment of topical condition, for example, darkened skin including age spots, circles around eyes and stretch marks; acne including excess facial oil and facial pore size; premature hair aging including hair loss and graying; inflammation including intra-cellular and extra-cellular inflammation; skin aging including wrinkles and fine lines; loss of collagen including thinning skin and loss of skin pliability; malfunction of tyrosinase group of enzymes; malfunction of matrix metalloprotease group of enzymes; and combinations thereof via the method of their topical application disclosed herein.

N-[(Hydroxyaryl)alkylidene]amino acid, in the present invention, is selected from N-[(2,4-Dihydroxyphenyl)ethylidene]glycine, N-[(2,4-Dihydroxyphenyl)ethylidene]histidine, N-[(2,4-Dihydroxyphenyl)ethylidene]carnosine, N-[(2,4-Dihydroxyphenyl)ethylidene]glutathione, N-[(2,4-Dihydroxyphenyl)ethylidene]arginine, N-[(2,4-Dihydroxyphenyl)ethylidene]tyrosine, N-[(2,4-Dihydroxyphenyl)ethylidene]phenylalanine, N-[(2,4-Dihydroxyphenyl)ethylidene]hydroxyphenylglycine, N-[(2,4-Dihydroxyphenyl)ethylidene]proline, N-[(2,4-Dihydroxyphenyl)ethylidene]lysine, N-[(2,4-Dihydroxyphenyl)ethylidene]tryptophane, N-[(2,4-Dihydroxyphenyl)ethylidene]serine, N-[(2,4-Dihydroxyphenyl)ethylidene]dihydroxytyrosine, N-[(2,4-Dihydroxyphenyl)ethylidene]cysteine, N-[(2,4-Dihydroxyphenyl)ethylidene]cystine, and N-[(2,4-Dihydroxyphenyl)ethylidene]methionine, N-[(2,5-Dihydroxyphenyl)ethylidene]glycine, N-[(2,5-Dihydroxyphenyl)ethylidene]histidine, N-[(2,5-Dihydroxyphenyl)ethylidene]carnosine, N-[(2,5-Dihydroxyphenyl)ethylidene]glutathione, N-[(2,5-Dihydroxyphenyl)ethylidene]arginine, N-[(2,5-Dihydroxyphenyl)ethylidene]tyrosine, N-[(2,5-Dihydroxyphenyl)ethylidene]phenylalanine, N-[(2,5-Dihydroxyphenyl)ethylidene]hydroxyphenylglycine, N-[(2,5-Dihydroxyphenyl)ethylidene]proline, N-[(2,5-Dihydroxyphenyl)ethylidene]lysine, N-[(2,5-Dihydroxyphenyl)ethylidene]tryptophane, N-[(2,5-Dihydroxyphenyl)ethylidene]serine, N-[(2,5-Dihydroxyphenyl)ethylidene]dihydroxytyrosine, N-[(2,5-Dihydroxyphenyl)ethylidene]cysteine, N-[(2,5-Dihydroxyphenyl)ethylidene]cystine, N-[(2,6-Dihydroxyphenyl)ethylidene]methionine, N-[(2,6-Dihydroxyphenyl)ethylidene]glycine, N-[(2,6-Dihydroxyphenyl)ethylidene]histidine, N-[(2,6-Dihydroxyphenyl)ethylidene]carnosine, N-[(2,6-Dihydroxyphenyl)ethylidene]glutathione, N-[(2,6-Dihydroxyphenyl)ethylidene]arginine, N-[(2,6-Dihydroxyphenyl)ethylidene]tyrosine, N-[(2,6-Dihydroxyphenyl)ethylidene]phenylalanine, N-[(2,6-Dihydroxyphenyl)ethylidene]hydroxyphenylglycine, N-[(2,6-Dihydroxyphenyl)ethylidene]proline, N-[(2,6-Dihydroxyphenyl)ethylidene]lysine, N-[(2,6-Dihydroxyphenyl)ethylidene]tryptophane, N-[(2,6-Dihydroxyphenyl)ethylidene]serine, N-[(2,6-Dihydroxyphenyl)ethylidene]dihydroxytyrosine, N-[(2,6-Dihydroxyphenyl)ethylidene]cysteine, N-[(2,6-Dihydroxyphenyl)ethylidene]cystine, N-[(2,6-Dihydroxyphenyl)ethylidene]methionine, N-{1-[(2-beta-D-Glucopyranosyloxy-4,6-dihydroxyphenyl)-3-(4-hydroxyphenyl]propylidene}glycine, N-[(2,4-Dihydroxyphenyl)ethylidene]proline, N-[(2,4-dihydroxyphenyl)ethylidene]hydroxyproline, N-[(2-beta-D-Glucopyranosyloxy-4,6-dihydroxyphenyl)-3-(4-hydroxyphenyl]propylidene}serine, N-{1-[(2-beta-D-Glucopyranosyloxy-4,6-dihydroxyphenyl)-3-(4-hydroxyphenyl]propylidene}carnosine, N-{1-[(2-beta-D-Glucopyranosyloxy-4,6-dihydroxyphenyl)-3-(4-hydroxyphenyl]propylidene}glutathione, N-{1-[(2-beta-D-Glucopyranosyloxy-4,6-dihydroxyphenyl)-3-(4-hydroxyphenyl]propylidene}proline, N-{1-[(2-beta-D-Glucopyranosyloxy-4,6-dihydroxyphenyl)-3-(4-hydroxyphenyl]propylidene}hydroxyproline, and N-{1-[(2,4,6-trihydroxyphenyl)-3-(4-hydroxyphenyl)]propylidene}glycine, and salts thereof.

The derivatives of an aldehyde or ketone with a primary amine, called (alkylidene)amino acids), or Schiff's bases, have been used extensively in chemical synthesis, for example, in peptide synthesis [Sheehan et al., Journal of American Chemical Society, vol. 84, 2417 (1962); Dane et al., Angew. Chemie, vol 74, 873 (1962)], and Al-Sayyab et al., J. Chem. Soc.(C), 406 (1968).

Asolkar et al., [Journal of Natural Products, vol. 48, 2 (2002)] have reported a natural Schiff's base, Limnazine. A copper chelated hydroxyalkyl ketone complex, Tenuazoic acid, is the only known example of a natural product of this class.

The Schiff's base complexes of metals are also well known in the prior art. Such complexes have been used, for example, in chemical synthesis, for example, as complexing agents [Johnson et al., Inorganic Chemistry, vol. 35, 2602 (1996); Can, Journal of Chemical Society, Perkin Trans. I, 3137 (1991)]; amine synthesis (Larm, U.S. Pat. No. 4,810,784); and cysteinyl protease inhibitors (Munoz et al., U.S. Pat. No. 6,617,426). The Schiff's base complexes of metals have usually been made in the prior art by the reaction of a Schiff's base with an inorganic metal salt, for example, Abd-Elzaher [Journal of the Chinese Chemical Society, vol. 48 153 (2001)] discloses Ni, Cu, and Zn complexes of Schiff's bases from 2-hydroxyacetophenone and aromatic diamines by such process.

The Schiff's bases of certain aromatic aldehydes with amino acid amides have been disclosed (U.S. Pat. Nos. 6,846,955; 5,047,585; 4,847,412; 4,172,846; and 4,873,359).

Martinez et al. (Journal of Materials Online, vol. 2, 1 (2006)] disclose nickel complexes of Schiff's bases derived from nitro-benzaldehyde and ethylenediamine. These have been used for certain electrode applications.

Keypour et al. [Journal of the Iranian Chemical Society, vol. 1, 53 (2004] disclose cadmium Schiff's base complexes prepared by the condensation of diacetylpyridine with hexamines, followed by the metalation of resulting Schiff's base derivative.

Gao et al. [Molecules, vol. 7, 511 (2002)] disclose certain Schiff's base ligands derived from 2-hydroxyacetophenone and chiral diamines suitable for metal complexation. These are not derived from amino acids.

Raman et al. [Journal of Chemical Science, vol. 4, 215 (2004)] disclose certain copper, cobalt, nickel, and zinc complexes of Schiff's bases derived from benzyl-2,4-dinitrophenylhydrazone with aniline. These have been of use as complexing agents in analytical chemistry.

Alemi et al. [Acta Chimica Slovenia, vol. 47, 363 (2000)] disclose certain copper complexes of Schiff's bases of butyl-calix[4]arenas.

Mandlik et al. [Polish Journal of Chemistry, vol. 77, 129 (2003)] disclose Cr, Mn, Fe, oxo-V, Zr, and dioxo-U complexes of Schiff's bases derived from 2,5-dihydroxyacetophenone and isonicotinoyl hydrazone. These were tested for potential antimicrobial activity. Other Hydroxyacetophenone derivatives, such as Phloridzin and Phloretin, which are known for their antioxidant and free-radical scavenging benefits (Gaudout et al., U.S. Pat. No. 7,041,322), have not been disclosed in their Schiff's base derivative forms.

Schiff's base derivatives of 2-hydroxyacetophenone and diaminodiphenylether have been disclosed for their x-ray analysis [Pinar et al., Acta Crystallographica, vol. E62, 2056 (2006)].

Copper complexes of Schiff's bases from 2-hydroxyacetophenone and hexamethylene thiosemicarbazide have been disclosed for their x-ray analysis [Sreekanth et al., Spectrochimica Acta, A Mol. Biomol. Spectroscop, vol. 59 1349 (2003)].

Copper complexes of 2-hydroxybenzophenone have been disclosed (Johnson, U.S. Pat. No. 4,361,667).

Kordosky et al. (U.S. Pat. Nos. 5,470,552; 4,507,268) disclose certain metal complexes of alkyl Hydroxyacetophenone oximes.

Schiff's bases from 2-hydroxyacetophenone and 2-methyl-1,3-phenylenediamine have been disclosed [Jarrahpour et al., Molbank, M455 (2006)]. Trace metal complexes of Schiff's bases have traditionally been made by a two step process in the prior art encompassing, (1) first, the preparation of the Schiff's base, and (2) second, the reaction of Schiff's base with a metal donor to form metal complex of Schiff's base.

The Schiff's bases, or N-[(Hydroxyaryl)alkylidene]amino acids [FIG. 1], of the present invention have now been prepared by a novel method. A mixture of hydroxyaryl alkyl ketone, an amino acid, and water is heated with mixing. N-[(Hydroxyaryl)alkylidene]amino acids are formed in-situ. This is both surprising and unexpected, since the preparation of said Schiff's bases of hydroxyaryl alkyl ketone and amino acid also results in the formation of a molecule of water. These reactions are thus usually performed in the prior art in an anhydrous medium in the absence of water, for example, Jarrahpour et al., Molbank, M455 (2006); Gao et al., Molecules, 7, 511 (2002). Moreover, the removal of water generated in this reaction by azeotropic distillation is frequently required. This reaction is accelerated by the inclusion of a monovalent metal oxide, metal hydroxide, metal carbonate, or metal bicarbonate in equimolar amounts to amino acid, in which case the monovalent salts of N-[(Hydroxyaryl)alkylidene]amino acids are formed, from which N-[(Hydroxyaryl)alkylidene]amino acids can be generated by the acidification of said monovalent salts to pH of 6.5 or less [FIG. 5]. In addition to amino acids, peptides can also be used in this reaction. The reaction of a hydroxyaryl alkyl ketone with a peptide in the presence of a monovalent metal oxide, metal hydroxide, metal carbonate, or metal bicarbonate in equimolar amounts results in the formation of the corresponding metal salt of N-[(Hydroxyaryl)alkylidene]peptide. For example, the reaction of a hydroxyaryl alkyl ketone with carnosine, a dipeptide, is illustrated in [FIG. 5].

[FIG. 5].

The trace metal complexes of Schiff's bases [FIG. 2] have been made in the present invention also by a novel chemical reaction between a (hydroxyaryl)alkyl ketone and a divalent or polyvalent metal complex of an amino acid, for example, as in FIG. 6. The reaction in FIG. 6 can be via a one step (Path A) or two-step (Path B) process. Irrespective of the process pathway (A), or (B), the end result is the same.

[FIG. 6].

The amino acid moiety can be an alpha-amino acid, a beta-amino acid, a gamma-amino acid, a delta amino acid, an epsilon amino acid, and so forth, although an alpha-amino acid is preferred.

However, if a monovalent metal complex of an amino acid is used in the above process then an open chain complex is obtained (Structure A, FIG. 2). The monovalent metal salt of an amino acid can be formed in situ, for example, by the reaction of a monovalent metal oxide, metal hydroxide, metal carbonate, or metal bicarbonate with an amino acid in equimolar amounts in water or a hydroxylic solvent. This reaction can be done in situ. For example, a metal oxide, metal hydroxide, metal carbonate, or metal bicarbonate is mixed with an amino acid in equimolar amounts in water solution, then a hydroxyaryl alkyl ketone is added and the mixture is heated to form monovalent metal salt of N-[(Hydroxyaryl) alkylidene]amino acid. The free-acid form of N-[(Hydroxyaryl)alkylidene]amino acid can be generated from the corresponding monovalent metal complex by adjusting the pH to 6.5 or less. This reaction can be monitored by ir spectroscopy. The principal bands in some of the N-[(2,4-Dihydroxyphenyl)ethylidene]amino acids are tabulated in Table 1.

TABLE 1

| Ir Spectral Data of N-[(2,4-Dihydroxyphenyl)ethylidene]amino acid [FIG. 1]. | | |
|---|---|---|
| Amino Acid | —C=N— | —C—O— |
| Glycine | 1601 | 1272 |
| Phenylalanine | 1596 | 1265 |
| Arginine | 1601 | 1271 |
| Cysteine | 1603 | 1272 |

Surprisingly and unexpectedly, a cyclic crown-like (FIG. 3) complex is obtained when a divalent or a polyvalent metal derivative of an amino acid is used (Structure B and C, respectively, FIG. 2). In terms of the reaction speeds, the reaction of a (hydroxyaryl)alkyl ketone and an amino acid or a metal complex of an amino acid is in the following order.

Divalent or polyvalent metal complex of amino acid >monovalent metal complex of amino acid >amino acid.

This reaction can be monitored by ir spectroscopy. For example, the reaction of copper glycinate with Resacetophenone in hydro-alcoholic medium results in the formation of N-[(2,4-Dihydroxyphenyl)ethylidene]glycine copper complex ("complex"), as in FIG. 7, Structure C. It is very likely solvated with alcohol at this state. The blue color of copper glycinate is replaced by bluish green color, followed by the precipitation of the complex as green to bluish green solid in this reaction. The ir bands of —CO—CH3 group of Resacetophenone at 1625 cm-1 is shifted downfield to 1606 cm-1 for the imine, —C=N—, group in the complex, and —COOH group of copper glycinate at 1612 cm-1 is shifted downfield to 1570 cm-1 in the complex. Also, a new band appears at 1525 cm-1 (—C=C—, aromatic) in the complex (1593 cm-1 in resacetophenone). Raman et al. have also noted a similar downfield shift of ir band of imine group, —C=N—, when complexed with a metal ion. The Cu—O—C— band present in copper glycinate at 1139 cm-1 is shifted to 1136 cm-1 in the complex. The preparation of this compound in water, in the absence of ethanol, provides its non-solvated form (see Example 3). The reaction with Phloridzin or Phloretin proceeds in a similar manner (FIG. 7, Structure D). Also, the plant extracts that contain hydroxyaryl alkyl ketones, for example, peony extract, which contains Paeonol;

Primula extract, which contains Resacetophenone; licorice extract (*Glycyrrhiza Glabra*), which contains isoliquiritigenin; and Apple root extract, which contains Phloridzin; can also be used in this reaction.

Principal ir bands in some of the N-[(2,4-Dihydroxyphenyl)ethylidene]glycine metal complexes are tabulated in Table 2.

TABLE 2

Ir Spectral Data of N-[(2,4-Dihydroxyphenyl)ethylidene]glycine Metal Complexes.

| Metal | —C=N->M | —C—O—M | —C—O (Phenolic) |
|---|---|---|---|
| Cu | 1605 | 1240, 860 | 1386 |
| Zn | 1624 | 1252, 844 | 1370 |
| Mn | 1599 | 1280, 908 | 1330 |
| Cr | 1603 | 1268, 804 | 1374 |
| Fe | 1605 | 1279, 771 | 1381 |

The ir data in Table 1 are in conformance to data reported by Crespi et al. [Quimica Nova, vol. 22, 41 (1999)] and Brezina et al. [Acta Universitat Palackianae Olomucensis, Chemica 37, 1 (1998)].

[FIG. 7].

The reaction of (hydroxyaryl)alkyl ketone with a divalent or polyvalent metal complex of amino acid is almost instantaneous. This may be due to very high structural stability that is obtained from the cyclized, crown-like complex ("Crown Complex") compared to the corresponding open chain structure. In a surprising and unexpected discovery, it has now been found that the reaction of a monovalent metal complex of an N-[(Hydroxyaryl)alkylidene]amino acid with a metal donor of a divalent or a polyvalent metal atom leads to a spontaneous formation of "Crown Complex", possibly via an intermediate reaction state (Route A, FIG. 8).

Additionally, via a yet another novel route, these "Crown Complexes" can also be made by the reaction of a divalent or polyvalent metal complex of a (hydroxyaryl)alkyl ketone with an amino acid, for example, for the reaction of resacetophenone copper complex with glycine to form N-[(2,4-Dihydroxyphenyl)ethylidene]glycine copper complex (Route B, FIG. 8). The complexes of the present invention can also be made by the reaction of a metal derivative of a hydroxyaryl alkyl ketone with an amino acid. This reaction can also be done in situ by the addition of a metal oxide, hydroxide, or carbonate to a mixture of said hydroxyaryl alkyl ketone in water or a hydroxylic solvent, followed by the addition of an amino acid and subsequent heating with mixing.

[FIG. 8].

Regardless of the chemical accuracy of the chemical name or chemical "Crown Complex" structure stated in the present invention for these very complicated molecules the utility of the present invention or of these novel molecules is not diminished in any manner. It is to be stated that the complexes of the present invention are in no way related to the cyclic polyether crown complexes.

The divalent or polyvalent metal donor of Ti, V, Cr, Mn, Fe, Co, Ni, Cu, Zn, Se, and Mo can be selected from a large number of compounds, for example, copper donors include copper chloride, copper sulfate, copper nitrate, copper acetate, copper glycinate, copper histidinate, copper amino acid chelate, copper peptide, copper gluconate, copper ketoglutarate, copper arginate, copper ascorbate, copper aspartate, copper caprylate, copper citrate, copper cysteinate, copper fumarate, copper glutamate, copper glycerophosphate, copper lactate, copper lysinate, copper malate, copper methionate, copper niacinate, copper picolinate, copper proteinate, copper pyruvate, copper salicylate, copper succinate, copper tartrate, copper yeast complex, and combinations thereof. Zinc donor include zinc chloride zinc sulfate, zinc nitrate, zinc acetate, zinc glycinate, zinc histidinate, zinc amino acid chelate, zinc peptide, zinc gluconate, zinc ketoglutarate, zinc arginate, zinc ascorbate, zinc aspartate, zinc caprylate, zinc citrate, zinc cysteinate, zinc fumarate, zinc glutamate, zinc glycerophosphate, zinc lactate, zinc lysinate, zinc malate, zinc methionate, zinc niacinate, zinc picolinate, zinc proteinate, zinc pyruvate, zinc salicylate, zinc succinate, zinc tartrate, zinc yeast complex, and combinations thereof. Manganese donors include manganese chloride manganese sulfate, manganese nitrate, manganese acetate, manganese glycinate, manganese histidinate, manganese amino acid chelate, manganese peptide, manganese gluconate, manganese ketoglutarate, manganese arginate, manganese ascorbate, manganese aspartate, manganese caprylate, manganese citrate, manganese cysteinate, manganese fumarate, manganese glutamate, manganese glycerophosphate, manganese lactate, manganese lysinate, manganese malate, manganese methionate, manganese niacinate, manganese picolinate, manganese proteinate, manganese pyruvate, manganese salicylate, manganese succinate, manganese tartrate, manganese yeast complex, and combinations thereof. These metal donors of amino acids can also be made in situ by the reaction of an amino acid with a metal hydroxide, metal carbonate, metal oxide, metal salt, or metal chelate.

The process for the metal complex of an N-[(Hydroxyaryl)alkylidene]amino acid, having general chemical structure in FIG. 2, comprises (i) the mixing at 50 to 120 C of (ii) a hydroxyaryl alkyl ketone and, (iii) a metal derivative of an amino acid, and (iv) a solubilizing agent. The hydroxyaryl alkyl ketone is selected from 2-hydroxyacetophenone, 3-hydroxyacetophenone, 4-hydroxyacetophenone, 2,3-dihydroxyacetophenone, 2,4-dihydroxyacetophenone, 2,5-dihydroxyacetophenone, 2,6-dihydroxyacetophenone, 3,4-dihydroxyacetophenone, 3,5-dihydroxyacetophenone, 2,4,6-trihydroxyacetophenone, 2,3,4-trihydroxyacetophenone, 2,3,5-trihydroxyacetophenone, 2,3,6-trihydroxyacetophenone, 2,4,5-trihydroxyacetophenone, 3,4,5-trihydroxyacetophenone, Resacetophenone, 2-Acetyl resorcinol, 4-Acetyl resorcinol, 3,4-Dihydroxyacetophenone, acetyl quinol, Phloridzin, Phloretin, Quinacetophenone, 1-(3-Hydroxy-4-methoxy-5-methylphenyl)ethanone, 1-(3-hydroxy-4-methoxyphenyl)ethanone, Paeonol, 2-hydroxypropiophenone, 3-hydroxypropiophenone, 4-hydroxypropiophenone, 2,3-dihydroxypropiophenone, 2,4-dihydroxypropiophenone, 2,5-dihydroxypropiophenone, 2,6-dihydroxypropiophenone, 3,4-dihydroxypropiophenone, 3,5-dihydroxypropiophenone, 2,4,6-trihydroxypropiophenone, 2,3,4-trihydroxypropiophenone, 2,3,5-trihydroxypropiophenone, 2,3,6-trihydroxypropiophenone, 2,4,5-trihydroxypropiophenone, and 3,4,5-trihydroxypropiophenone. Also, the plant extracts that contain hydroxyaryl alkyl ketones, for example, peony extract, Primula extract, and Apple root extract, can also be used in this process. The metal derivative of an amino acid is selected from Sodium, or potassium, or lithium, or calcium, or magnesium, or iron, or copper, or zinc, or manganese, or chromium, or cobalt, or selenium, or vanadium, or molybdenum complexed with glycine, or alanine, or beta-alanine, or valine, or leucine, or isoleucine, or phenylalanine, or alpha-amino butyric acid, or C-phenylglycine, or C-hydroxyphenylglycine, or proline, or tryptophane, or lysine, or ornithine, or arginine, or histidine, or citrulline, or glutamic acid, or aspartic acid, or serine, or threonine, or hydroxyproline, or tyrosine, or dihydroxytyrosine, or cysteine, or cystine, or methionine, or homocysteine, or lanthionine, or 5-amino levulinic acid, or a substituted amino acid. The solubilizing agent is selected from water, ethanol, glycerin, ethylene glycol, propylene glycol, butylene glycol, hexylene glycol, pyrrolidone, N-methylpyrrolidone, dimethyl sulfoxide, dimethyl sulfone, polyethylene glycol, polypropylene glycol, methylpropanediol, Triethyl citrate, and such.

Also, the reaction of (hydroxyaryl)alkyl ketone with a divalent or polyvalent metal complex of amino acid can be performed in a single step via a novel in-situ process. In the preparation of a skin lotion or cream composition, for example, all other ingredients of the said composition can be mixed and processed and the (hydroxyaryl)alkyl ketone and a divalent or polyvalent metal complex of amino acid can then be added to the composition. Wherein the corresponding "Crown Complex" is spontaneously formed in-situ. The addition or mixing order of various ingredients can be in any order or sequence. Additionally, (hydroxyaryl)alkyl ketone can first be reacted with the monovalent metal salt of an amino acid to form the open chain structure (Structure A, FIG. 2), which than can be transformed into the corresponding "Crown Complex" (Structure B, FIG. 2) via its reaction with a divalent or polyvalent metal donor. These multi-step reaction sequences can be performed in a single step via the in-situ process of the present invention.

The hydroxyaryl ketones used in the present invention can be from various sources, such as from chemical synthesis or from natural origin such as plants, various plant parts (leaf, root, flower, bark, seed, et cetera). Hydroxyaryl alkyl ketones are well known from the plant sources, for example, Primula obconica was introduced to Europe from Hubei, China in 1880, and has been cultivated worldwide as one of popular ornamental plants. Primula obconica extract has been shown to contain acetyl hydroquinone and methyl acetyl hydroquinone [Nan et al., Z. Naturforsch., 58, 57-61 (2003)]. Peony root bark (*Paeonia Suffruticosa Radix*) contains high levels of Paeonol (2-Hydroxy-4-methoxy acetophenone). Apple root contains Phloridzin and Phloretin. The extracts, both in crude form or in highly refined form, are suitable for applications of the present invention. The chemical names of "Crown Complexes" from such botanical extracts can be simplified, for example, for INCI (International Nomenclature for cosmetic Ingredients) listings. The "Crown Complex" from Phloridzin and copper glycinate, for example, can be identified as Phloridzin Glycine Copper Complex. The "Crown Complex" from Apple root extracts and copper glycinate can be identified as *Pyrus Alba* (Apple Root) Glycine Copper Complex. The "Crown Complex" from Peony root extract can be identified as Paeonia Suffruticosa Glycine Copper Complex. The "Crown Complex" from Primula extract can be identified as Primula Obconica Glycine Copper Complex.

The present invention also discloses a method for topical application of N-[(Hydroxyaryl)alkylidene]amino acids and metal complexes thereof, either in combination or alone, having general chemical structure in FIG. 1 and FIG. 2, respectively, and wherein (i) a hydroxyaryl alkyl ketone, and (ii) an amino acid, or a metal derivative thereof, and (iii) water are mixed at 50 to 95C to form said N-[(Hydroxyaryl)alkylidene] amino acid, or metal complex thereof, respectively, and (iv) the topical application of said N-[(Hydroxyaryl)alkylidene] amino acid or metal complex thereof. This method can include a composition, or a base or a carrier. This method provides a number of topical benefits, which includes skin whitening, skin wrinkles reduction, acne control, facial oil control, hair loss modulation, and hair graying reduction.

Organic copper complexes have found applications in medical field. Daniel et al., Biochemical Pharmacology, vol. 7, 1139 (2004) report proteasome-inhibiting benefits of 8-hydroxyquinoline copper (II). Meares et al (U.S. Pat. No. 4,678, 667) disclose polyamine complexes of copper useful for serum diagnostic applications. About 30 elements are recognized as essential to life. Trace metals, in general, are required for body functions. Some are required in macroscopic amounts in essentially all forms of life: H, Na, K, Mg, Ca, C, N, O, P, S, and Cl. The others occur in trace or ultratrace quantities. Fe, Cu, and Zn are at the top end of this "trace" scale. The other elements required are Li, B, F, Si, V, Cr, Mn, Co, Ni, As, Se, Mo, W, and I. The trace and ultratrace metals most important for human cellular functions are Fe, Cu, Zn, Mn, Co, Cr, V, and Se. In human body there are about 4 to 6 grams of iron, 2 to 3 grams of zinc, and only 250 mg of copper. Cobalt is found in Vitamin B12. There is one cobalt atom in this vitamin; the latter is present in only 2 to 5 mg quantity in the human body.

The present invention relates to certain Schiff's bases of natural amino acids, N-[(Hydroxyaryl)alkylidene]amino acids, having general chemical structure in FIG. 1 for topical application. The present invention also relates to certain trace metal complex of such Schiff's bases, which have a crown-like appearance in their three-dimensional chemical structure, as shown in FIG. 2. The Schiff's bases and their trace metal complexes of the present invention, surprisingly and unexpectedly, are useful for the modulation of metal-activated enzymes and metalloenzymes, specifically Phenylalanine Hydroxylase, Tyrosine Transaminase, Phenylalanine Transaminase, Tyrosinase, MMP (Matrix metalloproteases), and Superoxide dismutase. Surprisingly and unexpectedly, the compositions of the present invention are further suitable for topical methods for skin whitening, skin wrinkles reduction, skin antiaging, acne control, hair loss prevention, and hair graying control.

Inhibition of Phenylalanine Hydroxylase and Phenylalanine Transaminase.

The biosynthetic pathways from shikimic acid leading to the formation of melanin are summarized in FIG. 9 that will be used as a reference for subsequent discussions.

[FIG. 9].

Phenylalanine hydroxylase is responsible for the first step in the conversion of phenylalanine into tyrosine. Tyrosine is required for the production of melanin, which gives color to hair and skin. Phenylalanine hydroxylase must work in combination with tetrahydrobiopterin to perform this function. Phenylalanine hydroxylase contains iron in its active site, and tetrahydrobiopterin is required in proximity to this active site, as shown in FIG. 10.

[FIG. 10].

It is both surprising and unexpected that N-[(Hydroxyaryl) alkylidene]amino acids of the present invention inhibit phenylalanine hydroxylase. Although the mechanism of this inhibition is not fully clear at this time, it is theorized that the chelation of iron metal at the active site of Phenylalanine hydroxylase (Reaction Step 8, FIG. 9) by N-[(Hydroxyaryl) alkylidene]amino acids could be the cause of this effect. The structure of proposed iron metal binding chelate is shown in FIG. 11.

[FIG. 11].

It is also possible that N-[(Hydroxyaryl)alkylidene]amino acids may be acting as competitive substrates for phenyl pyruvate for phenylalanine biosynthesis[Reaction Step 4, FIG. 9], thus inhibiting the synthesis of phenylalanine. The structural similarity of phenyl pyruvate, in its enolic form (Structure F), with N-[(Hydroxyaryl)alkylidene]amino acids (Structure E) is shown in FIG. 12. Irrespective of the actual mechanism, the discovery that N-[(Hydroxyaryl)alkylidene] amino acids of the present invention inhibit the synthesis of tyrosine from phenylalanine or its precursor is unprecedented in the prior art.

[FIG. 12].

Inhibition of Tyrosine Transaminase and Monophenol Monooxygenase (Tyrosinase).

The inhibition of melanin synthesis can also be achieved via the inhibition of tyrosine transaminase (inhibition of amination of hydroxyphenyl Pyruvate or phenyl Pyruvate (Step [7] and/or [4], FIG. 9), which leads to eventual inhibition of tyrosine biosynthesis. The melanin synthesis can also be blocked by the inhibition of monophenol monooxygenase (EC 1.14.18.1), which converts tyrosine into dopaquinone via the intermediacy of dopa (FIG. 13). In a surprising and unexpected discovery, the N-[(hydroxyphenyl)ethylidene]amino acids and their zinc or manganese complexes of the present invention inhibit both tyrosine transaminase and monophenol monooxygenase (biochemical steps in FIG. 13). The precise mechanism of this inhibition is not known at this time, but it is hypothesized that the N-[(hydroxyphenyl)ethylidene] amino acids and their Zn and Mn complexes of the present invention act as competitive substrates for the enzymes themselves or the enzyme-substrate bound states. The Zn and Mn complexes of N-[(hydroxyphenyl)ethylidene]amino acids may also be acting as inhibitors via the replacement of Cu or Fe in the active-site of monophenol monooxygenase. Also, N-[(hydroxyphenyl)ethylidene]amino acids may be complexing with the Cu—Cu active site of tyrosinase, thus deactivating that enzyme. Regardless of the actual biochemical mechanism the importance of this invention remains unexpected and novel.

[FIG. 13].

Inhibition of Matrix Metalloproteases (MMP).

Matrix metalloproteases (MMP) are naturally-occurring enzymes found in most mammals and are zinc-dependent endopeptidases that perform extracellular tissue reorganization (matrix reorganization). One major biological function of the matrix metalloprotease (MMP) is to catalyze the breakdown of connective tissue or extracellular matrix by virtue of their ability to hydrolyze various components of the tissue or matrix. Examples of the components that may be hydrolyzed by an MMP include collagens (for example, Collagenases type I, II, III, or IV), gelatins (for example, Gelatinases), proteoglycans, and fibronectins. Apart from their role in degrading connective tissue, MMPs are also involved in the activation of the zymogen (pro) forms of other MMPs thereby inducing MMP activation (proenzyme activation). They are also involved in the biosynthesis of TNF-alpha which is implicated in many pathological conditions and can cause or contribute to the effects of inflammation, rheumatoid arthritis, asthma, COPD, autoimmune disease, multiple sclerosis, graft rejection, fibrotic disease, cancer, infectious diseases, malaria, mycobacterial infection, meningitis, fever, psoriasis, cardiovascular/pulmonary effects (e.g., post-ischemic reperfusion injury), congestive heart failure, hemorrhage, coagulation, hyperoxic alveolar injury, radiation damage, cachexia, anorexia, and acute phase responses like those seen with infections and sepsis and during shock (e.g., septic shock and hemodynamic shock).

Over 30 MMPs have been characterized so far in humans and several major groups have been determined based on substrate specificity, some of which are described below, and are believed applicable to the present invention.

MMP-1 (also known as collagenase 1, or fibroblast collagenase). The substrates of MMP-1 include collagen I, collagen II, collagen III, gelatin, and proteoglycans. Over-expression of this enzyme is believed to be associated with emphysema, with hyperkeratosis and atherosclerosis, overexpressed alone in papillary carcinoma.

MMP-2 (also known as gelatinase A, basement membrane collagenase, or proteoglycanase). The substrates of MMP-2 include collagen I, collagen II, collagen IV, collagen V, collagen VII, collagen X, collagen XI, collagen XIV, elastin, fibronectin, gelatin, nidogen, believed to be associated with tumor progression through specificity for type IV collagen (high expression observed in solid tumors and believed to be associated with their ability to grow, invade, develop new blood vessels and metastasize) and to be involved in acute lung inflammation and in respiratory distress syndrome.

MMP-3 (also known as stromelysin 1). The substrates of MMP-3 include collagen III, collagen IV, collagen V, collagen IX, collagen X, laminin, nidogen, overexpression believed to be involved in atherosclerosis, aneurysm and restenosis.

MMP-7 (also known as matrilysin). The substrates of MMP-7 include collagen IV, elastin, fibronectin, gelatin, laminin.

MMP-8 (also known as collagenase 2, or neutrophil collagenase). The substrates of MMP-8 include collagen I, collagen II, collagen III, collagen V, collagen VII, collagen IX, gelatin over-expression of which can lead to non-healing chronic ulcers.

MMP-9 (also known as gelatinase B, or 92 kDa gelatinase). The substrates of MMP-9 include collagen I, collagen III, collagen IV, collagen V, collagen VII, collagen X, collagen XIV, elastin, fibronectin, gelatin, nidogen The above enzyme is believed to be associated with tumor progression through specificity for type IV collagen, to be released by eosinophils in response to exogenous factors such as air pollutants, allergens and viruses, to be involved in the inflammatory response in asthma and to be involved in acute lung inflammation and respiratory distress syndrome. The applicants believe that an inhibitor for this enzyme would be effective in the treatment of chronic obstructive pulmonary disorder (COPD) and/or asthma.

MMP-10 (also known as stromelysin 2). The substrates of MMP-10 include collagen III, collagen IV, collagen V, elastin, fibronectin, and gelatin.

MMP-11 (also known as stromelysin 3). The substrates of MMP-11 include serine protease inhibitors (Serpins).

MMP-12 (also known as metalloelastase, human macrophage elastase, or HME). The substrates of MMP-12 include fibronectin, laminin, believed to play a role in tumor growth inhibition and regulation of inflammation and to play a pathological role in emphysema and in atherosclerosis, aneurysm and restenosis. The applicants believe that an inhibitor for this enzyme would be effective in the treatment of chronic obstructive pulmonary disorder (COPD) and/or asthma.

MMP-13 (also known as collagenase 3). The substrates of MMP-13 include collagen I, collagen II, collagen III, collagen IV, collagen IX, collagen X, collagen XIV, fibronectin, and gelatin, recently identified as being over-expressed alone in breast carcinoma. The applicants believe that an inhibitor for this enzyme would be effective in the treatment of breast cancer and arthritis.

MMP-14 (also known as membrane MMP or MT1-MMP). The substrates of MMP-14 include MMP-2, collagen I, collagen II, collagen III, fibronectin, gelatin, laminin.

MMP-15 (also known as MT2-MMP). The substrates of MMP-15 include MMP-2, collagen I, collagen II, collagen III, fibronectin, laminin nidogen.

MMP-16 (also known as MT3-MMP). The substrates of MMP-16 include MMP-2, collagen I, collagen III, and fibronectin.

MMP-17 (also known as MT4-MMP), substrates fibrin (fibrinogen).

MMP-18 (also known as collagenase 4).

MMP-19 (also known as Rasi-1). The substrates of MMP-19 include MMP-9, gelatin, laminin-1, collagen IV, and fibronectin.

MMP-20 (also known as enamelysin), substrate amelogenin.

MMP-23 (also known as femalysin), substrate gelatin.

MMP-24 (also known as MT5-MMP). The substrates of MMP-24 include MMP-2, gelatin, fibronectin, chondroitin, and dermitin sulfate proteoglycans.

MMP-25 (also known as MT6-MMP). The substrates of MMP-25 include MMP-2, gelatin, collagen IV, and fibronectin.

MMP-26 (also known as matrilysin 2 or endometase). The substrates of MMP-26 include denatured collagen, fibrinogen, fibronectin, vitronectin.

MMP-28; also known as epilysin, substrates caesin.

Over-activation of a matrix metalloprotease ("MMP"), or an imbalance between an MMP and a natural (i.e., endogenous) tissue inhibitor of a matrix metalloprotease ("TIMP"), has been linked to the pathogenesis of diseases characterized by the breakdown of connective tissue or extracellular matrix. Examples of diseases characterized by over-expression and/or over-activation of an MMP include rheumatoid arthritis, asthma, COPD, osteoarthritis; osteoporosis; periodontitis; multiple sclerosis; gingivitis; corneal, epidermal, and gastric ulceration; atherosclerosis; neointimal proliferation, which leads to restenosis and ischemic heart failure; stroke; renal disease; macular degeneration; and tumor metastasis.

Further, some MMP-mediated diseases may involve over activity of only one MMP enzyme. This is supported by the recent discovery that MMP-13 alone is over-expressed in breast carcinoma, while MMP-1 alone is over-expressed in papillary carcinoma.

Research has been carried out into the identification of inhibitors that are selective, for example, for a few of the MMP subtypes. A MMP inhibitor of improved selectivity would avoid potential side effects associated with inhibition of MMPs that are not involved in the pathogenesis of the disease being treated. Further, use of more selective MMP inhibitors would require administration of a lower amount of the inhibitor for treatment of disease than would otherwise be required and, after administration, partitioned in vivo among multiple MMPs. Still further, the administration of a lower amount of compound would improve the margin of safety between the dose of the inhibitor required for therapeutic activity and the dose of the inhibitor at which toxicity is observed. Some of these approaches have been discussed by Gupta (U.S. patent application Ser. No. 20060074108), who also discloses MMP inhibitors based on certain Aryl alkyl ketones. Gupta also discusses prior art references that clearly show that the problem of selective MMP modulation is not yet solved. In a surprising and unexpected discovery, N-[(Hydroxyaryl)alkylidene]amino acids and their trace metal complexes have now been found to selectively inhibit various MMP.

The precise mechanism by which the MMP of the present invention operate is not known. In one aspect, the present invention provides a compound that is a matrix metalloprotease inhibitor, and that (a) binds into at least one or both of the Zinc binding sites of MMP to effect the spatial distortion of such active-sites, and (b) exhibits selectivity for a matrix metalloprotease or group of matrix metalloproteases, and (c) detaches itself from the bound state with the zinc center of the active-site of MMP after distorting its spatial configuration, and (d) repeats the cycle for effecting the spatial distortion of the active-site of additional MMP. The spatial distortion of zinc active-site may be caused by the electron donating hydroxyl group of hydroxyaryl moiety of N-[(Hydroxyaryl)alkylidene]amino acid. In any event, these results are both surprising and unexpected, irrespective of the actual mechanism of such MMP inhibitory effects elicited by the compounds of the present invention.

Antioxidant affect by the activation of superoxide dismutase (SOD). One of the major roles played by trace elements in human biochemistry is in metalloenzymes. This term is applied to enzymes that not only require the participation of a metal ion at the active site to function but bind that metal ion or ions strongly even in the resting stage (F. A. Cotton and G. Wilkinson, Advanced Inorganic Chemistry, Fifth Edition, John Wiley, 1988). Known metalloenzymes now number several hundred. The role of metal atoms in enzymatic catalysis is currently an active area of research.

Metalloenzymes may be considered as a subclass of the metalloproteins. Metalloproteins are proteins that incorporate one or more metal atoms as a normal part of their structure. This includes not only metalloenzymes but also respiratory proteins like hemoglobin and myoglobin, electron transport proteins such as cytochromes and ferredoxins, and metal storage proteins.

In many cases it is possible to remove the metal atoms and then restore them or replace them by others without collapse of the overall protein structure. The protein from which the metal ions have been removed is called the apoprotein, the use of this term usually implying that the active metalloprotein can be recovered on restoration of the metal ions.

In recent years it has become clear that transition metal such as Cu, Zn, Mn, Cr, Co, and Se are essential for normal development and function of human cells. Copper is the third most abundant trace element in human body, with vitamin-like impact on living systems. Copper functions as a cofactor in over 30 enzymes. The ability of copper to cycle between oxidized $Cu^{2+}$ and a reduced $Cu^+$ state is used by cuproenzymes involved in redox reactions, the two most important examples being Cu/Zn superoxide dismutase and cytochrome C oxidase. Cu/Zn Superoxide dismutase (SOD) is an important enzyme responsible for the destruction of toxic superoxide anion in human body that directly relates to the processes of skin aging and inflammation. The enhancement or increment of SOD functions for antiaging and anticancer benefits is of current scientific and consumer interest. Some of these aspects have recently been disclosed by several authors in recently published text books, such as Valentine et al. [(Advances in Protein Chemistry, vol. 60, pp. 93-121, Academic Press, CA (2002)]; and Massaro [(Handbook of Copper Pharmacology and Toxicology, Humana Press, NJ (2002)], which are quoted here only for reference. It has also become clear that ATP, a major nucleotide present in human body, plays a major role in copper transport, in the form of copper transporting ATPase enzyme, that utilizes the energy of ATP-hydrolysis to transport copper from the cytosol through various cell membranes [Tsivkovskii et al. (J. Biol. Chem., 277, 976-983 (2002); Nakayama et al. (Oncology Reports, 8, 1285-1287 (2001); Wunderli-Ye et al. (Biochem. Biophys. Res. Commun., 280, 713-719 (2001)]. These disclosures point to possible importance of nucleotide complexes of copper in the bioavailability and intra-cellular transport of copper in humans. Despite the obviousness of this, the methods for the topical application or penetration of such nucleotide complexes of trace metals remain unknown in the prior art. Wijnhoven et al. (U.S. Pat. No. 6,277,605) disclose an interesting role of divalent metals, such as copper, zinc, and manganese, in the complexation with DNA molecules that results in the bond distance increase of nucleic acid components, resulting in the annealing of the DNA helix. A simple oxidation-reduction step of such divalent metal ions can cause annealing or reannealing of such separated DNA strands. This indicates a prospective application of copper zinc, and manganese complexes of nucleic acids, nucleosides, and nucleotides in cosmetic and biomedical control of the process of skin aging. The methods for the topical delivery or penetration of such essential trace metals by such complexes, despite their obvious need, have been unknown in the prior art.

Of over 30 enzymes that require copper in their active site, superoxide dismutase is most important from the viewpoint of skin aging and inflammation. Superoxide dismutase (SOD) is one of the enzymes that are most directly linked to superoxide anion detoxification, and, as its production slows down, the process of aging accelerates. Among other biologically important cuproenzymes, the formation of elastin and collagen is a function of amine oxidase, which is another example of a copper-containing metalloenzyme. The skin pigmentation, or melanin formation, is a function of tyrosinase, which is a copper-based monooxygenase class of metalloenzyme. Ceruloplasmin, a copper-containing metalloenzyme, has a role in the iron transport in human body. Dopamine hydroxylase, another copper-based metalloenzyme, is present in adrenal glands, and it converts dopamine to norepinephrine. SOD occurs in three distinct forms in mammalian systems; (i) SOD containing copper and zinc (CuZnSOD, SOD1), which is usually located in the cytosol; (ii) SOD containing manganese (MnSOD, SOD2), which is usually located in mitochondria (MnSOD); and (iii) Another SOD containing Cu and Zn (CuZnSOD, SOD3), which is found in extra-cellular spaces. Additionally, many bacterial SOD contain iron.

In mammalian systems, CuZnSOD (SOD1) catalyses the dismutation of the superoxide anion radical (O2-.), as shown in [FIG. 14].

[FIG. 14].

One product of this reaction, $H_2O_2$, is also a harmful substance. Hydrogen peroxide is detoxified by catalase, a heme iron metalloenzyme. The superoxide anion (O2-.) exhibits numerous physiological toxic effects including endothelial cell damage, increased micro vascular permeability, formation of chemotactic factors such as leukotrienes, recruitment of neurophils at the sites of inflammation, lipid peroxidation, and oxidation, release of cytokines, DNA single-strand damage, and formation of peroxynitrite anion ($ONO_2$—.), a potent cytotoxic and pro-inflammatory molecule. Excess superoxide anion can also lead to the formation of highly oxidizing species such as hydroxide and peroxide radicals. Superoxide radical anion, and the peroxynitrite anion formed in its reaction with NO, cause cell death from ischemic tissue. Most of these physiological effects lead to skin aging and tissue degeneration [(Macarthur et al., Proc. Natl. Acad. Sci. USA, 97, 9753-9758 (2000)]. In this capacity, SOD acts as an antioxidant inhibiting aging and carcinogenesis.

In a surprising and unexpected discovery, Cu, Zn, and Mn complexes of N-[(Hydroxyaryl)alkylidene]amino acids of the present invention activate SOD. Although the exact biochemical mechanism is still unknown, it is possible that N-[(Hydroxyaryl)alkylidene]amino acids act as transporters of Cu, Zn, and Mn to the active site of SOD. Regardless of the actual mechanism, the activation of SOD by the trace metal complexes of N-[(Hydroxyaryl)alkylidene]amino acids of the present invention is unprecedented in the prior art.

Hair Loss and Hair Graying Prevention.

Hair and nail are rich in keratin. Keratin biosynthesis requires a source for sulfur, which is usually provided by cysteine, cystine, or methionine. The bioavailability of these water-soluble amino acids is poor from many topical applications that require a rinse step. Lower production of keratin can lead to thinning and fragile hair.

The hair graying is caused by a loss of Tyrosinase activity, leading to lessened synthesis of melanin in hair.

It is also well known that MMP enzymes become more activated with aging. The over activation of MMP leads to increased inflammation at the hair bulb that causes hair loss. This has been documented in prior art, for example, Jarrousse et al., U.S. Pat. No. 6,645,477; Wang et al., U.S. patent application Ser. No. 20020037827; Dublanchet et al., U.S. patent application Ser. No. 20040171543 and 2003017523; de Almeida et al., Arch. Dermatol Res. 297, 121 (2005); Jarrousse et al., Int. J. Dermatol., 40, 385 (2001); and Yamazaki et al., J. Investig Dermatol Symp Proc. 4, 312 (1999).

Also with aging, the use of harsh chemicals and bleaching agents, and frequent hair combing the hair tends to develop split ends. The split ends in hair are caused by the breakage of disulfide bond in cystine moiety of hair protein keratin.

In a surprising and unexpected discovery, the N-[(Hydroxyaryl)alkylidene]amino acids, in which amino acid is selected from cysteine, cystine, or methionine, and their trace metal complexes derived from Cu, Zn, or Mn, for example [FIG. 15], have shown hair loss prevention, anti-graying of hair, and hair split end repair benefits.

[FIG. 15].

N-[(Hydroxyaryl)alkylidene]amino acids, in which amino acid is selected from cysteine, cystine, or methionine, have now been found to strongly inhibit several MMP, including MMP-1, MMP-2, MMP-9, MMP-13, and MMP-25 in hair bulb, the aging-related up-regulation of all of which is known to cause hair loss due to increased loss of connective tissue that holds hair bulb to scalp skin.

The copper complexes of N-[(Hydroxyaryl)alkylidene] amino acids, in which amino acid is selected from cysteine, cystine, or methionine, have now been found to provide a dual benefit. These provide the activation of Tyrosinase, possibly by their donation of copper to Tyrosinase active-site, and the down-regulation of MMP. These biochemical mechanisms then lead to both hair loss prevention and hair graying prevention.

The copper complexes of N-[(Hydroxyaryl)alkylidene] amino acids, in which amino acid is selected from cysteine, cystine, or methionine, have now been found to also repair split ends. This is very likely from the binding of "crown complexes" with the —SH groups that have been generated by the splitting of —S—S— group of cystine, as illustrated in [FIG. 16] and [FIG. 17]. The role of metal atoms of "Crown Complexes" in crosslinking of —SH group of cysteine in hair is unprecedented.

[FIG. 16].

[FIG. 17].

It is thus unprecedented that a combination of several highly desirable benefit for hair are obtained from the present surprising and unexpected discovery of N-[(Hydroxyaryl) alkylidene]amino acids, in which amino acid is selected from cysteine, cystine, or methionine.

Skin Brightening and Antiwrinkle—Antiaging Applications.

N-[(Hydroxyaryl)alkylidene]amino acids of the present invention provide an unexpected inhibition of MMP, tyrosinase, and tyrosine biosynthesis enzymes. The down-regulation of MMP leads to reduced degradation of connective issue such as collagen and fibrin. This results in increased suppleness of skin, leading to reduced visible skin winkles from aging. The decreased biosynthesis of tyrosine and dopa, and inhibition of Tyrosinase and tyrosine precursor enzymes leads to skin brightening effects, all of which are both surprising and unexpected when taken as a group of such desirable benefits. In normal practice, such group of desirable benefits is usually achievable only from a combination of several ingredients. It is thus unexpected and surprising that just one ingredient, such as an N-[(Hydroxyaryl)alkylidene] amino acid, can provide multiple desirable topical benefits. The exact biochemical mechanism for these unexpected benefits is not yet known.

Facial Oil and Acne Control.

Acne is caused by, among other factors, excess facial oil production. This oil is broken down into lower molecular weight fatty acids by topical bacteria and fungi. Those fatty acids cause inflammation. The facial oil is produced via de novo synthesis of fatty acids in sebacious glands from acetyl coenzyme A via citrate lyase. Citrate lyase is known to contain arginine residues at its active site (Ramakrishna et al., Biochem. J., 195, 735 (1981). The blocking of this arginine residue also causes the inhibition of citrate lyase. It is also known that the deactivation or suppression of "molybdenum cofactor" causes the activation of citrate lyase. (Clark, FEMS Microbiol Lett., 55, 245 (1990). Molybdopterin is one of such "Molybdenum cofactor" agents [FIG. 18].

[FIG. 18].

Molybdenum-containing enzymes catalyze basic metabolic reactions in the nitrogen, sulfur, and carbon cycles. With the exception of the nitrogenase cofactor, molybdenum is incorporated into proteins as the molybdenum cofactor that contains a mononuclear molybdenum atom coordinated to the sulfur atoms of a pterin derivative named molybdopterin. Certain microorganisms can also utilize tungsten in a similar fashion. Molybdenum-cofactor-containing enzymes catalyze the transfer of an oxygen atom, ultimately derived from or incorporated into water, to or from a substrate in a two-electron redox reaction. On the basis of sequence alignments and spectroscopic properties, four families of molybdenum-cofactor-containing enzymes have been identified. The available crystallographic structures for members of these families are discussed within the framework of the active site structure and catalytic mechanisms of molybdenum-cofactor-containing enzymes. Although the function of the molybdopterin ligand has not yet been conclusively established, interactions of this ligand with the coordinated metal are sensitive to the oxidation state, indicating that the molybdopterin may be directly involved in the enzymatic mechanism [C. Kisker et al., Annual Rev Biochemistry, 66, 233 (1997)]. Molybdenum cofactor is the cofactor for four human enzymes: xanthine dehydrogenase (xanthine: $NAD^+$ oxidoreductase), xanthine oxidase (a form of xanthine dehydrogenase), sulfite oxidase (sulfite dehydrogenase; sulfite: ferricytochrome c oxidoreductase), and aldehyde oxidase (aldehyde: oxygen oxidoreductase).

It is possible that molybdenum binds with arginine in the active site of citrate lyase, which thus causes its inhibition. The removal of molybdenum by other agents can thus cause, at least theoretically, the activation of citrate lyase. Conversely, the supply of molybdenum to the active site can cause the deactivation of citrate lyase. In a surprising an unexpected discovery, the molybdenum complexes of N-[(Hydroxyaryl) alkylidene]amino acids, especially N-[(Hydroxyaryl)alkylidene]arginine, causes the inhibition of citrate lyase and also the inhibition of topical oil synthesis. N-[(Hydroxyaryl)alkylidene]amino acid molybdenum complexes are thus useful for anti-acne applications.

Zinc salts of certain polyhydroxy acids are well known for their anti-acne benefits. For example, Dreno et al. [Eur. J. Dermatol. 15, 152 (2005)] report zinc gluconate in controlling resistant variety of Propionibacteriaum acnes (acne bacteria). Maynerdier [Eur. J. Dermatol., 10, 269 (2000)] reports efficacy of zinc gluconate in the treatment of inflammatory acne. Stephan et al. [Ann. Dermatol. Verereol., 131, 455 (2004)] report zinc salts in dermatology. Dutiel et al. [Ann. Dermatol. Venereol., 132, 219 (2005)] report photosensitization potential of zinc gluconate for acne treatment. In a surprising and unexpected discovery, zinc complexes of N-[(Hydroxyaryl)alkylidene]amino acids of the present invention show superior anti-acne benefits over zinc gluconate.

The compositions of the present invention can be formulated in various cosmetic and pharmaceutical consumer products utilizing a variety of delivery systems and carrier bases. Such consumer product forms include the group consisting of shampoos, aftershaves, sunscreens, body and hand lotions, skin creams, liquid soaps, bar soaps, bath oil bars, shaving creams, conditioners, permanent waves, hair relaxers, hair bleaches, hair detangling lotion, styling gel, styling glazes, spray foams, styling creams, styling waxes, styling lotions, mousses, spray gels, pomades, shower gels, bubble baths, hair coloring preparations, conditioners, hair lighteners, coloring and non-coloring hair rinses, hair grooming aids, hair tonics, spritzes, styling waxes, band-aids, and balms.

In another preferred aspect, the delivery system or a carrier base are selected in the form of a lotion, cream, gel, spray, thin liquid, body splash, powder, compressed powder, tooth paste, tooth powder, mouth spray, paste dentifrice, clear gel dentifrice, mask, serum, solid cosmetic stick, lip balm, shampoo, liquid soap, bar soap, bath oil, paste, salve, collodion, impregnated patch, impregnated strip, skin surface implant, impregnated or coated diaper, and similar delivery or packaging form.

In another preferred aspect, the delivery system can be human body or hair deodorizing solution, deodorizing powder, deodorizing gel, deodorizing spray, deodorizing stick, deodorizing roll-on, deodorizing paste, deodorizing cream, deodorizing lotion, deodorizing aerosol, and other commonly marketed human body and hair deodorizing compositions, household deodorizing solution, deodorizing powder, deodorizing gel, deodorizing spray, carpet deodorizer, room deodorizer, and other commonly marketed household deodorizing compositions, animals and pets deodorizing solution, deodorizing powder, deodorizing gel, deodorizing spray, animals and pets carpet deodorizer, animals and pets room deodorizer, and other commonly marketed animal and pet deodorizing compositions.

In another preferred aspect, the delivery system can be traditional water and oil emulsions, suspensions, colloids, microemulsions, clear solutions, suspensions of nanoparticles, emulsions of nanoparticles, or anhydrous compositions.

Additional cosmetically or pharmaceutically beneficial ingredients can also be included in the formulated compositions of the present invention, which can be selected from, but not limited to skin cleansers, cationic, anionic surfactants, non-ionic surfactants, amphoteric surfactants, and zwitterionic surfactants, skin and hair conditioning agents, vitamins, hormones, minerals, plant extracts, anti-inflammatory agents, collagen and elastin synthesis boosters, UVA/UVB sunscreens, concentrates of plant extracts, emollients, moisturizers, skin protectants, humectants, silicones, skin soothing ingredients, antimicrobial agents, antifungal agents, treatment of skin infections and lesions, blood microcirculation improvement, skin redness reduction benefits, additional moisture absorbents, analgesics, skin penetration enhancers, solubilizers, moisturizers, emollients, anesthetics, colorants, perfumes, preservatives, seeds, broken seed nut shells, silica, clays, beads, luffa particles, polyethylene balls, mica, pH adjusters, processing aids, and combinations thereof.

In another preferred aspect, the cosmetically acceptable composition further comprises one or more excipient selected from the group consisting of water, saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines from about $C_{10}$ to $C_{22}$, long chain fatty amines from about $C_{10}$ to $C_{22}$, fatty alcohols, ethoxylated fatty alcohols and di-tail phospholipids.

Representative saccharides include nonionic or cationic saccharides such as agarose, amylopectins, amyloses, arabinans, arabinogalactans, arabinoxylans, carageenans, gum arabic, carboxymethyl guar gum, carboxymethyl(hydroxypropyl) guar gum, hydroxyethyl guar gum, carboxymethyl cellulose, cationic guar gum, cellulose ethers including methyl cellulose, chondroitin, chitins, chitosan, chitosan pyrrolidone carboxylate, chitosan glycolate chitosan lactate, cocodimonium hydroxypropyl oxyethyl cellulose, colominic acid ([poly-N acetyl-neuraminic acid]), corn starch, curdlan, dermatin sulfate, dextrans, furcellarans, dextrans, cross-linked dextrans, dextrin, emulsan, ethyl hydroxyethyl cellulose, flaxseed saccharide (acidic), galactoglucomannans, galactomainans, glucomannans, glycogens, guar gum, hydroxy ethyl starch, hydroxypropyl methyl cellulose, hydroxy ethyl cellulose, hydroxy propyl cellulose, hydroxypropyl starch, hydroxypropylated guar gums, gellan gum, gellan, gum ghatti, gum karaya, gum tragancanth (tragacanthin), heparin, hyaluronic acid, inulin, keratin sulfate, konjac mannan, modified starches, laminarans, laurdimonium hydroxypropyl oxyethyl cellulose, okra gum, oxidized starch, pectic acids, pectin, polydextrose, polyquaternium-4, polyquaternium-10, polyquaternium-28, potato starch, protopectins, psyllium seed gum, pullulan, sodium hyaluronate, starch diethylaminoethyl ether, steardimonium hydroxyethyl cellulose, raffinose, rhamsan, tapioca starch, whelan, levan, scleroglucan, sodium alginate, stachylose, succinoglycan, wheat starch, xanthan gum, xylans, xyloglucans, and mixtures thereof. Microbial saccharides can be found in Kirk-Othmer Encyclopedia of Chemical Technology, Fourth Edition, Vol. 16, John Wiley and Sons, NY pp. 578-611 (1994), which is incorporated entirely by reference. Complex carbohydrates found in Kirk-Othmer Encyclopedia of Chemical Technology, Fourth Edition, Vol. 4, John Wiley and Sons, NY pp. 930-948, 1995 which is herein incorporated by reference.

The cosmetically acceptable composition of this invention may include surface-active agents. Surface-active agents include surfactants, which typically provide detersive functionality to a formulation or act simply as wetting agents. Surface-active agents can generally be categorized as anionic surface-active agents, cationic surface-active agents, nonionic surface-active agents, amphoteric surface-active agents and zwitterionic surface-active agents, and dispersion polymers.

Anionic surface-active agents useful herein include those disclosed in U.S. Pat. No. 5,573,709, incorporated herein by reference. Examples include alkyl and alkyl ether sulfates.

Specific examples of alkyl ether sulfates which may be used In this invention are sodium and ammonium salts of lauryl sulfate, lauryl ether sulfate, coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 6 moles of ethylene oxide.

Another suitable class of anionic surface-active agents is the alkyl sulfuric acid salts. Important examples are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, for example, sulfur trioxide or oleum, obtained according to known sulfonation methods, including bleaching and hydrolysis. Preferred are alkali metals and ammonium sulfated $C_{12-38}$ n-paraffins.

Additional synthetic anionic surface-active agents include the olefin sulfonates, the beta-alkyloxy alkane sulfonates, and the reaction products of fatty acids esterified with isethionic acid and neutralized with sodium hydroxide, as well as succinamates. Specific examples of succinamates include disodium N-octadecyl sulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Preferred anionic surface-active agents for use in the cosmetically acceptable composition of this invention include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecylbenzene sulfonate.

Amphoteric surface-active agents which may be used in the cosmetically acceptable composition of this invention include derivatives of aliphatic secondary and tertiary amines, in which the aliphatic substituent contains from about 8 to 18 carbon atoms and an anionic water solubilizing group e.g., carboxy, sulfonate, sulfate, phosphate, or phosphonate. Representative examples include sodium 3-dodecyl-amino-propionate, sodium 3-dodecylaminopropane sulfonate, sodium lauryl sarcosinate, N-alkyltaurines such as the one prepared by reacting dodecylamine with sodium isethionate as described in U.S. Pat. No. 2,658,072, N-higher alkyl aspartic acids as described in U.S. Pat. No. 2,438,091, and the products sold under the trade name MIRANOL. as described in U.S. Pat. No. 2,528,378. Other sarcosinates and sarcosinate derivatives can be found in the CTFA Cosmetic Ingredient Handbook, Fifth Edition, 1988, page 42 incorporated herein by reference.

Quaternary ammonium compounds can also be used in the cosmetically acceptable composition of this invention as long as they are compatible in the compositions of the invention, wherein the structure is provided in the CTFA Cosmetic Ingredient Handbook, Fifth Edition, 1988, page 40. Cationic surface-active agents generally include, but are not limited to fatty quaternary ammonium compounds containing from about 8 to about 18 carbon atoms. The anion of the quaternary ammonium compound can be a common ion such as chloride, ethosulfate, methosulfate, acetate, bromide, lactate, nitrate, phosphate, or tosylate and mixtures thereof. The long chain alkyl groups can include additional or replaced carbon or hydrogen atoms or ether linkages. Other substitutions on the quaternary nitrogen can be hydrogen, hydrogen, benzyl or short chain alkyl or hydroxyalkyl groups such as methyl, ethyl, hydroxymethyl or hydroxyethyl, hydroxypropyl or combinations thereof.

Examples of quaternary ammonium compounds include but are not limited to: Behentrimonium chloride, Cocotrimonium chloride, Cethethyldimonium bromide, Dibehenyldimonium chloride, Dihydrogenated tallow benzylmonium chloride, disoyadimonium chloride, Ditallowedimonium chloride, Hydroxycetyl hydroxyethyl dimonium chloride, Hydroxyethyl Behenamidopropyl dimonium chloride, Hydroxyethyl Cetyldimonium chloride, Hydroxyethyl tallowedimonium chloride, myristalkonium chloride, PEG-2 Oleamonium chloride, PEG-5 Stearmonium chloride, PEG-15 cocoyl quaternium 4, PEG-2 stearalkonium 4, lauryltrimonium chloride; Quaternium-16; Quaternium-18, lauralkonium chloride, olealkmonium chloride, cetylpyridinium chloride, Polyquaternium-5, Polyquaternium-6, Polyquaternium-7, Polyquaternium-10, Polyquaternium-22, Polyquaternium-37, Polyquaternium-39, Polyquaternium-47, cetyl trimonium chloride, dilauryldimonium chloride, cetalkonium chloride, dicetyldimonium chloride, soyatrimonium chloride, stearyl octyl dimonium methosulfate, and mixtures thereof. Other quaternary ammonium compounds are listed in the CTFA Cosmetic Ingredient Handbook, First Edition, on pages 41-42, incorporated herein by reference.

The cosmetically acceptable compositions may include long chain fatty amines from about $C_{10}$ to $C_{22}$ and their derivatives. Specific examples include dipalmitylamine, lauramidopropyldimethylamine, and stearamidopropyl dimethylamine. The cosmetically acceptable compositions of this invention may also include fatty alcohols (typically monohydric alcohols), ethoxylated fatty alcohols, and di-tail phospholipids, which can be used to stabilize emulsion or dispersion forms of the cosmetically acceptable compositions. They also provide a cosmetically acceptable viscosity. Selection of the fatty alcohol is not critical, although those alcohols characterized as having fatty chains of $C_{10}$ to $C_{32}$, preferably $C_{14}$ to $C_{22}$, which are substantially saturated alkanols will generally be employed. Examples include stearyl alcohol, cetyl alcohol, cetostearyl alcohol, myristyl alcohol, behenyl alcohol, arachidic alcohol, isostearyl alcohol, and isocetyl alcohol. Cetyl alcohol is preferred and may be used alone or in combination with other fatty alcohols, preferably with stearyl alcohol. When used the fatty alcohol is preferably included in the formulations of this invention at a concentration within the range from about 1 to about 8 weight percent, more preferably about 2 to about 6 weight percent. The fatty alcohols may also be ethoxylated. Specific examples include cetereth-20, steareth-20, steareth-21, and mixtures thereof. Phospholipids such as phosphatidylserine and phosphatidylcholine, and mixtures thereof may also be included. When used, the fatty alcohol component is included in the formulations at a concentration of about 1 to about 10 weight percent, more preferably about 2 to about 7 weight percent.

Nonionic surface-active agents, which can be used in the cosmetically acceptable composition of the present invention, include those broadly defined as compounds produced by the condensation of alkylene oxide groups (hydrophilic in nature) with an organic hydrophobic compound, which may be aliphatic or alkyl aromatic in nature. Examples of preferred classes of nonionic surface-active agents are: the long chain alkanolamides; the polyethylene oxide condensates of alkyl phenols; the condensation product of aliphatic alcohols having from about 8 to about 18 carbon atoms, in either straight chain or branched chain configuration, with ethylene oxide; the long chain tertiary amine oxides; the long chain tertiary phosphine oxides; the long chain dialkyl sulfoxides containing one short chain alkyl or hydroxy alkyl radical of from about 1 to about 3 carbon atoms; and the alkyl polysaccharide (APS) surfactants such as the alkyl polyglycosides; the polyethylene glycol (PEG) glyceryl fatty esters.

Zwitterionic surface-active agents such as betaines can also be useful in the cosmetically acceptable composition of this invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the RCONH $(CH_2)_3$ radical is attached to the nitrogen atom of the betaine are also useful in this invention.

The anionic, cationic, nonionic, amphoteric or zwitterionic surface-active agents used in the cosmetically acceptable composition of this invention are typically used in an amount from about 0.1 to 50 percent by weight, preferably from about 0.5 to about 40 percent by weight, more preferably from about 1 to about 20 percent by weight.

The cosmetically acceptable composition of this invention may include humectants, which act as hygroscopic agents, increasing the amount of water absorbed, held and retained. Suitable humectants for the formulations of this invention include but are not limited to: acetamide MEA, ammonium lactate, chitosan and its derivatives, colloidal oatmeal, galactoarabinan, glucose glutamate, glerecyth-7, glygeryth-12, glycereth-26, glyceryth-31, glycerin, lactamide MEA, lactamide DEA, lactic acid, methyl gluceth-10, methyl gluceth-20, panthenol, propylene glycol, sorbitol, polyethylene glycol, 1,3-butanediol, 1,2,6-hexanetriol, hydrogenated starch hydrolysate, inositol, mannitol, PEG-5 pentaerythritol ether, polyglyceryl sorbitol, xylitol, sucrose, sodium hyaluronate, sodium PCA, and combinations thereof. Glycerin is a particularly preferred humectant. The humectant is present in the composition at concentrations of from about 0.5 to about 40 percent by weight, preferably from about 0.5 to about 20 percent by weight and more preferably from about 0.5 to about 12 percent by weight.

The cosmetically acceptable composition of this invention may include petrolatum or mineral oil components, which when selected will generally be USP or NF grade. The petrolatum may be white or yellow. The viscosity or consistency grade of petrolatum is not narrowly critical. Petrolatum can be partially replaced with mixtures of hydrocarbon materials, which can be formulated to resemble petrolatum in appearance and consistency. For example, mixtures of petrolatum or mineral oil with different waxes and the like may be combined. Preferred waxes include bayberry wax, candelilla wax, ceresin, jojoba butter, lanolin wax, montan wax, ozokerite, polyglyceryl-3-beeswax, polyglyceryl-6-pentastearate, microcrystalline wax, paraffin wax, isoparaffin, vaseline solid paraffin, squalene, oligomer olefins, beeswax, synthetic candelilla wax, synthetic carnauba, synthetic beeswax and the like may be blended together. Alkylmethyl siloxanes with varying degrees of substitution can be used to increase water retained by the skin. Siloxanes such as stearyl dimethicone, known as 2503 Wax, C30-45 alkyl methicone, known as AMS-C30 wax, and stearoxytrimethylsilane (and) stearyl alcohol, known as 580 Wax, each available from Dow Corning, Midland, Mich., USA. Additional alkyl and phenyl silicones may be employed to enhance moisturizing properties. Resins such as dimethicone (and) trimethylsiloxysilicate or Cyclomethicone (and) Trimethylsiloxysilicate fluid, may be utilized to enhance film formation of skin care products. When used, the petrolatum, wax or hydrocarbon or oil component is included in the formulations at a concentration of about 1 to about 20 weight percent, more preferably about 1 to about 12 weight percent. When used, the silicone resins can be included from about 0.1 to about 10.0 weight percent.

Emollients are defined as agents that help maintain the soft, smooth, and pliable appearance of skin. Emollients function by their ability to remain on the skin surface or in the stratum corneum. The cosmetically acceptable composition of this invention may include fatty ester emollients, which are listed in the International Cosmetic Ingredient Dictionary, Eighth Edition, 2000, p. 1768 to 1773. Specific examples of suitable fatty esters for use in the formulation of this invention include isopropyl myristate, isopropyl palmitate, caprylic/capric triglycerides, cetyl lactate, cetyl palmitate, hydrogenated castor oil, glyceryl esters, hydroxycetyl isostearate, hydroxy cetyl phosphate, isopropyl isostearate, isostearyl isostearate, diisopropyl sebacate, PPG-5-Ceteth-20, 2-ethylhexyl isononoate, 2-ethylhexyl stearate, $C_{12}$ to $C_{16}$ fatty alcohol lactate, isopropyl lanolate, 2-ethyl-hexyl salicylate, and mixtures thereof. The presently preferred fatty esters are isopropyl myristate, isopropyl palmitate, PPG-5-Ceteth-20, and caprylic/capric triglycerides. When used the fatty ester emollient is preferably included in the formulations of this invention at a concentration of about 1 to about 8 weight percent, more preferably about 2 to about 5 weight percent.

The compositions of this invention may also include silicone compounds. Preferably, the viscosity of the silicone component is from about 0.5 to about 12,500 cps. Examples of suitable materials are dimethylpolysiloxane, diethylpolysiloxane, dimethylpolysiloxane-diphenylpolysiloxane, cyclomethicone, trimethylpolysiloxane, diphenylpolysiloxane, and mixtures thereof. Dimethicone, a dimethylpolysiloxane end blocked with trimethyl units, is one preferred example. Dimethicone having a viscosity between 50 and 1,000 cps is particularly preferred. When used, the silicone oils are preferably included in the formulations of this invention at a concentration of 0.1 to 5 weight percent, more preferably 1 to 2 weight percent.

The cosmetically acceptable compositions of this invention may include volatile and non-volatile silicone oils or fluids. The silicone compounds can be either linear or cyclic polydimethylsiloxanes with a viscosity from about 0.5 to about 100 centistokes. The most preferred linear polydimethylsiloxane compounds have a range from about 0.5 to about 50 centistokes. One example of a linear, low molecular weight, volatile polydimethylsiloxane is octamethyltrisiloxane-200 fluid having a viscosity of about 1 centistoke. When used, the silicone oils are preferably included in the formulations of this invention at a concentration of 0.1 to 30 weight percent, more preferably 1 to 20 weight percent.

The cosmetically acceptable compositions of this invention may include volatile, cyclic, low molecular weight polydimethylsiloxanes (cyclomethicones). The preferred cyclic volatile siloxanes can be polydimethyl cyclosiloxanes having an average repeat unit of 4 to 6, and a viscosity from about 2.0 to about 7.0 centistokes, and mixtures thereof. Preferred cyclomethicones are available from Dow Corning, Midland, Mich., and from General Electric, Waterford, N.Y., USA. When used, the silicone oils are preferably included in the formulations of this invention at a concentration of 0.1 to 30 weight percent, more preferably 1 to 20 weight percent.

Silicone surfactants or emulsifiers with polyoxyethylene or polyoxypropylene side chains may also be used in compositions of the current invention. Preferred examples include dimethicone copolyols and 5225C Formulation Aids, available from Dow Corning, Midland, Mich., USA and Silicone SF-1528, available from General Electric, Waterford, N.Y., USA. The side chains may also include alkyl groups such as lauryl or cetyl. Preferred are lauryl methicone copolyol. 5200 Formulation Aid, and cetyl dimethicone copolyol, known as Abil EM-90, available from Goldschmidt Chemical Corporation, Hopewell, Va. Also preferred is lauryl dimethicone, known as Belsil LDM 3107 VP, available from Wacker-Chemie, Munchen, Germany. When used, the silicone surfactants are preferably included in the formulations of this invention at a concentration of 0.1 to 30 weight percent, more preferably 1 to 15 weight percent. Amine functional silicones and emulsions may be utilized in the present invention. Preferred examples include Dow Corning 8220, Dow Corning 939, Dow Corning 949, Dow Corning 2-8194, all available from Dow Corning, Midland, Mich., USA. Also preferred is Silicone SM 253 available from General Electric, Waterford, N.Y., USA. When used, the amine functional silicones are preferably included in the formulations of this invention at a concentration of 0.1 to 5 weight percent, more preferably 0.1 to 2.0 weight percent.

The cosmetically acceptable compositions of this invention may include volatile hydrocarbon oils. The volatile hydrocarbon comprises from about $C_6$ to $C_{22}$ atoms. A preferred volatile hydrocarbon is an aliphatic hydrocarbon having a chain length from about $C_6$ to $C_{16}$ carbon atoms. An example of such compound includes isohexadecane, under the trade name Permethyl 101A, available from Presperse, South Plainfield, N.J., USA. Another example of a preferred volatile hydrocarbon is $C_{12}$ to $C_{14}$ isoparaffin, under the trade name Isopar M, available from Exxon, Baytown, Tex., USA. When used, the volatile hydrocarbons are preferably included in the formulations of this invention at a concentration of 0.1 to 30 weight percent, more preferably 1 to 20 weight percent.

The cosmetically acceptable compositions of this invention may include cationic and ampholytic conditioning polymers. Examples of such include, but are not limited to those listed by the International Cosmetic Ingredient Dictionary published by the Cosmetic, Toiletry, and Fragrance Association (CTFA), 1101 17 Street, N.W., Suite 300, Washington, D.C. 20036. General examples include quaternary derivatives of cellulose ethers, quaternary derivatives of guar, homopolymers and copolymers of DADMAC, homopolymers and copolymers of MAPTAC and quaternary derivatives of starches. Specific examples, using the CTFA designation, include, but are not limited to Polyquaternium-10, Guar hydroxypropyltrimonium chloride, Starch hydroxypropyltrimonium chloride, Polyquaternium-4, Polyquaternium-5, Polyquaternium-6, Polyquaternium-7, Polyquaternium-14, Polyquaternium-15, Polyquaternium-22, Polyquaternium-24, Polyquaternium-28, Polyquaternium-32, Polyquaternium-33, Polyquaternium-36, Polyquaternium-37, Polyquaternium-39, Polyquaternium-45, Polyquaternium-47 and polymethacrylamidopropyltrimonium chloride, and mixtures thereof. When used, the conditioning polymers are preferably included in the cosmetically acceptable composition of this invention at a concentration of from 0.1 to 10 weight percent, preferably from 0.2 to 6 weight percent and most preferably from 0.2 to 5 weight percent.

The cosmetically acceptable composition of this invention may include one or more rheological modifiers. The rheological modifiers that can be used in this invention include high molecular weight crosslinked homopolymers of acrylic acid, and Acrylates/C10-30 Alkyl Acrylate Crosspolymer, such as the Carbopol and Pemulen series, both available from B. F. Goodrich, Akron, Ohio, USA; anionic acrylate polymers such as Salcare and cationic acrylate polymers such as Salcare SC96, available from Ciba Specialties, High Point, N.C., USA; Acrylamidopropyltrimonium chloride/acrylamide; Hydroxyethyl methacrylates polymers, Steareth-10 Allyl Ether/Acrylate Copolymer; Acrylates/Beheneth-25 Metacrylate Copolymer, known as Aculyn, available from International Specialties, Wayne, N.J., USA; Glyceryl Polymethacrylate, Acrylates/Steareth-20 Methacrylate Copolymer; bentonite; gums such as alginates, carageenans, gum acacia, gum arabic, gum ghatti, gum karaya, gum tragacanth, guar gum; guar hydroxypropyltrimonium chloride, xanthan gum or gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol, PVM/MA copolymer, PVM/MA decadiene crosspolymer, poly(ethylene oxide) based thickeners, sodium carbomer, and mixtures thereof. When used, the rheology modifiers are preferably included in the cosmetically acceptable composition of this invention at a concentration of from 0.01 to 12 weight percent, preferably from 0.05 to 10 weight percent and most preferably from 0.1 to 6 weight percent.

The cosmetically acceptable composition of this invention may include one or more antioxidants, which include, but are not limited to ascorbic acid, BHT, BHA, erythorbic acid, bisulfite, thioglycolate, tocopherol, sodium metabisulfite, vitamin E acetate, and ascorbyl palmitate. The anti oxidants will be present at from 0.01 to 20 weight percent, preferably 0.5 to 10 weight percent and most preferably from 1.0 to 5.0 weight percent of the cosmetically acceptable composition.

The cosmetically acceptable composition of this invention may include one or more sunscreen active agents. Examples of sunscreen active agents include, but are not limited to octyl methoxycinnamate (ethylhexyl p-methoxycinnamate), octyl salicylate oxybenzone (benzophenone-3), benzophenone-4, menthyl anthranilate, dioxybenzone, aminobenzoic acid, amyl dimethyl PABA, diethanolamine p-methoxy cinnamate, ethyl 4-bis(hydroxypropyl) aminobenzoate, 2-ethylhexy 1-2-cyano-3,3-diphenylacrylate, homomethyl salicylate, glyceryl aminobenzoate, dihydroxyacetone, octyl dimethyl PABA, 2-phenylbenzimidazole-5-sulfonic acid, triethanolamine salicylate, zinc oxide, and titanium oxide, and mixtures thereof. The amount of sunscreen used in the cosmetically acceptable composition of this invention will vary depending on the specific UV absorption wavelength(s) of the specific sunscreen active(s) used and can be from 0.1 to 10 percent by weight, from 2 to 8 percent by weight.

The cosmetically acceptable composition of this invention may include one or more preservatives. Example of preservatives, which may be used include, but are not limited to 1,2-dibromo-2,4-dicyano butane (Methyldibromo Glutaronitrile, known as MERGUARD. Nalco Chemical Company, Naperville, Ill., USA), benzyl alcohol, imidazolidinyl urea, 1,3-bis(hydroxymethyl)-5,5-dimethyl-2,3-imidazolidinedione (e.g., DMDM Hydantoin, known as GLYDANT, Lonza, Fairlawn, N.J., USA.), methylchloroisothiazolinone and methylisothiazolinone (e.g., Kathon, Rohm & Haas Co., Philadelphia, Pa., USA), methyl paraben, propyl paraben, phenoxyethanol, and sodium benzoate, and mixtures thereof.

The cosmetically acceptable composition of this invention may include any other ingredient by normally used in cosmetics. Examples of such ingredients include, but are not limited to buffering agents, fragrance ingredients, chelating agents, color additives or dyestuffs which can serve to color the composition itself or keratin, sequestering agents, softeners, foam synergistic agents, foam stabilizers, sun filters and peptizing agents.

The surface of pigments, such titanium dioxide, zinc oxide, talc, calcium carbonate or kaolin, can be treated with the unsaturated quaternary ammonium compounds described herein and then used in the cosmetically acceptable composition of this invention. The treated pigments are then more effective as sunscreen actives and for use in color cosmetics such as make up and mascara.

The cosmetically acceptable composition of this invention can be presented in various forms. Examples of such forms include, but are not limited a solution, liquid, cream, emulsion, dispersion, gel, thickening lotion.

The cosmetically acceptable composition of this invention may contain water and also any cosmetically acceptable solvent. Examples of acceptable solvents include, but are not limited to monoalcohols, such as alkanols having 1 to 8 carbon atoms (like ethanol, isopropanol, benzyl alcohol and phenylethyl alcohol) polyalcohols, such as alkylene glycols (like glycerin, ethylene glycol and propylene glycol) and glycol ethers, such as mono-, di- and tri-ethylene glycol monoalkyl ethers, for example ethylene glycol monomethyl ether and diethylene glycol monomethyl ether, used singly or in a mixture from 0.1 to 70 percent by weight, relative to the weight of the total composition.

The cosmetically acceptable composition of this invention can also be packaged as an aerosol, in which case it can be applied either in the form of an aerosol spray or in the form of an aerosol foam. As the propellant gas for these aerosols, it is possible to use, in particular, dimethyl ether, carbon dioxide, nitrogen, nitrous oxide, air and volatile hydrocarbons, such as butane, isobutane, and propane.

The cosmetically acceptable composition of this invention also can contain electrolytes, such as aluminum chlorohydrate, alkali metal salts, e.g., sodium, potassium or lithium salts, these salts preferably being halides, such as the chloride or bromide, and the sulfate, or salts with organic acids, such as the acetates or lactates, and also alkaline earth metal salts, preferably the carbonates, silicates, nitrates, acetates, gluconates, pantothenates and lactates of calcium, magnesium and strontium.

Compositions for treating skin include leave-on or rinse-off skin care products such as lotions, hand/body creams, shaving gels or shaving creams, body washes, sunscreens, liquid soaps, deodorants, antiperspirants, suntan lotions, after sun gels, bubble baths, hand or mechanical dishwashing compositions, and the like. In addition to the polymer, skin care compositions may include components conventionally used in skin care formulations. Such components include for example; (a) humectants, (b) petrolatum or mineral oil, (c) fatty alcohols, (d) fatty ester emollients, (e) silicone oils or fluids, and (f) preservatives. These components must in general be safe for application to the human skin and must be compatible with the other components of the formulation. Selection of these components is generally within the skill of the art. The skin care compositions may also contain other conventional additives employed in cosmetic skin care formulations. Such additives include aesthetic enhancers, fragrance oils, dyes and medicaments such as menthol and the like.

The skin care compositions of this invention may be prepared as oil-in-water, water-in-oil emulsions, triple emulsions, or dispersions.

Preferred oil-in-water emulsions are prepared by first forming an aqueous mixture of the water-soluble components, e.g. unsaturated quaternary ammonium compounds, humectants, water-soluble preservatives, followed by adding water-insoluble components. The water-insoluble components include the emulsifier, water-insoluble preservatives, petrolatum or mineral oil component, fatty alcohol component, fatty ester emollient, and silicone oil component. The input of mixing energy will be high and will be maintained for a time sufficient to form a water-in-oil emulsion having a smooth appearance (indicating the presence of relatively small micelles in the emulsion). Preferred dispersions are generally prepared by forming an aqueous mixture of the water-soluble components, followed by addition of thickener with suspension power for water-insoluble materials.

Compositions for treating hair include bath preparations such as bubble baths, soaps, and oils, shampoos, conditioners, hair bleaches, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products. The dispersion polymers may also be utilized in styling type leave-in products such as gels, mousses, spritzes, styling creams, styling waxes, pomades, balms, and the like, either alone or in combination with other polymers or structuring agents in order to provide control and hair manageability with a clean, natural, non-sticky feel.

Hair care compositions of this invention give slippery feel and that can be easily rinsed from the hair due to the presence of the dispersion polymer, volatile silicones, other polymers, surfactants or other compounds that may alter the deposition of materials upon the hair.

In the case of cleansing formulations such as a shampoo for washing the hair, or a liquid hand soap, or shower gel for washing the skin, the compositions contain anionic, cationic, nonionic, zwitterionic or amphoteric surface-active agents typically in an amount from about 3 to about 50 percent by weight, preferably from about 3 to about 20 percent, and their pH is general in the range from about 3 to about 10.

Preferred shampoos of this invention contain combinations of anionic surfactants with zwitterionic surfactants and/or amphoteric surfactants. Especially preferred shampoos contain from about 0 to about 16 percent active of alkyl sulfates, from 0 to about 50 weight percent of ethoxylated alkyl sulfates, and from 0 to about 50 weight percent of optional surface-active agents selected from the nonionic, amphoteric, and zwitterionic surface-active agents, with at least 5 weight percent of either alkyl sulfate, ethoxylated alkyl sulfate, or a mixture thereof, and a total surfactant level of from about 10 weight to about 25 percent.

The shampoo for washing hair also can contain other conditioning additives such as silicones and conditioning polymers typically used in shampoos. U.S. Pat. No. 5,573,709 provides a list of non-volatile silicone conditioning agents that can be used in shampoos. The conditioning polymers for use with the present invention are listed in the Cosmetic, Toiletries and Fragrance Associations (CTFA) dictionary. Specific examples include the Polyquaterniums (example Polyquaternium-1 to Polyquaternium-50), Guar Hydroxypropyl Trimonium Chloride, Starch Hydroxypropyl Trimonium Chloride and Polymethacrylamidopropyl Trimonium Chloride.

Other preferred embodiments consist of use in the form of a rinsing lotion to be applied mainly before or after shampooing. These lotions typically are aqueous or aqueous-alcoholic solutions, emulsions, thickened lotions or gels. If the compositions are presented in the form of an emulsion, they can be nonionic, anionic or cationic. The nonionic emulsions consist mainly of a mixture of oil and/or a fatty alcohol with a polyoxyethyleneated alcohol, such as polyoxyethyleneated stearyl or cetyl/stearyl alcohol, and cationic surface-active agents can be added to these compositions. The anionic emulsions are formed essentially from soap.

If the compositions are presented in the form of a thickened lotion or a gel, they contain thickeners in the presence or absence of a solvent. The thickeners which can be used are especially resins, Carbopol-type acrylic acid thickeners available from B.F. Goodrich; xanthan gums; sodium alginates; gum arabic; cellulose derivatives and poly-(ethylene oxide) based thickeners, and it is also possible to achieve thickening by means of a mixture of polyethylene glycol stearate or distearate or by means of a mixture of a phosphoric acid ester and an amide. The concentration of thickener is generally 0.05 to 15 percent by weight. If the compositions are presented in the form of a styling lotion, shaping lotion, or setting lotion, they generally comprise, in aqueous, alcoholic or aqueous-alcoholic solution, the ampholyte polymers defined above.

In the case of hair fixatives, the composition may also contain one or more additional hair fixative polymers. When present, the additional hair fixative polymers are present in a total amount of from about 0.25 to about 10 percent by weight. The additional hair fixative resin can be selected from the following group as long as it is compatible with a given dispersion polymer: acrylamide copolymer, acrylamide/sodium acrylate copolymer, acrylate/ammonium methacrylate copolymer, an acrylate copolymer, an acrylic/acrylate copolymer, adipic acid/dimethylaminohydroxypropyl diethylenetriamine copolymer, adipic acid/epoxypropyl diethylenetriamine copolymer, allyl stearate/VA copolymer, aminoethylacrylate phosphate/acrylate copolymer, an ammonium acrylate copolymer, an ammonium vinyl acetate/acrylate copolymer, an AMP acrylate/diacetoneacrylamide copolymer, an AMPD acrylate/diacetoneacrylamide copolymer, butyl ester of ethylene/maleic anhydride copolymer, butyl ester of PVM/MA copolymer, calcium/sodium PVM/MA copolymer, corn starch/acrylamide/sodium acrylate copolymer, diethylene glycolamine/epichlorohydrin/piperazine-copolymer, dodecanedioic acid/cetearyl alcohol/glycol copolymer, ethyl ester of PVM/MA copolymer, isopropyl ester of PVM/MA copolymer, karaya gum, a methacryloyl ethyl betaine/methacrylate copolymer, an octylacrylamide/acrylate/butylaminoethyl methacrylate copolymer, an octylacrylamide/acrylate copolymer, phthalic anhydride/glycerin/glycidyl decanoate copolymer, a phthalic/trimellitic/glycol copolymer, polyacrylamide, polyacrylamidomethylpropane sulfonic acid, polybutylene terephthalate, polyethylacrylate, polyethylene, polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-39, polyquaternium-47, polyvinyl acetate, polyvinyl butyral, polyvinyl imidazolinium acetate, polyvinyl methyl ether, PVM/MA copolymer, PVP, PVP/dimethylaminoethylmethacrylate copolymer, PVP/eicosene copolymer, PVP/ethyl methacrylate/methacrylic acid copolymer, PVP/hexadecene copolymer, PVP/VA copolymer, PVP/vinyl acetate/itaconic acid copolymer, shellac, sodium acrylates copolymer, sodium acrylates/Acrylnitrogens copolymer, sodium acrylate/vinyl alcohol copolymer, sodium carrageenan, starch diethylaminoethyl ether, stearylvinyl ether/maleic anhydride copolymer, sucrose benzoate/sucrose acetate isobutyrate/butyl benzyl phthalate copolymer, sucrose benzoate/sucrose acetate isobutyrate/butyl benzyl phthalate/methyl methacrylate copolymer, sucrose benzoate/sucrose acetate isobutyrate copolymer, a vinyl acetate/crotonate copolymer, vinyl acetate/crotonic acid copolymer, vinyl acetate/crotonic acid/methacryloxybenzophenone-1 copolymer, vinyl acetate/crotonic acid/vinyl neodecanoate copolymer, and mixtures thereof. Synthetic polymers used for creating styling aids are described in "The History of Polymers in Haircare," Cosmetics and Toiletries, 103 (1988), incorporated herein by reference. Other synthetic polymers that may be used with the present invention can be referenced in the CTFA Dictionary, Fifth Edition, 2000, incorporated herein by reference.

The cosmetic compositions of this invention may be formulated in a wide variety of form, for non-limited example, including a solution, a suspension, an emulsion, a paste, an ointment, a gel, a cream, a lotion, a powder, a soap, a surfactant-containing cleanser, an oil, a powder foundation, an emulsion foundation, a wax foundation and a spray. In detail, the cosmetic composition of the present invention can be provided in a form of skin softener (skin lotion), astringent lotion, nutrient emulsion (milk lotion), nutrient cream, message cream, essence, eye cream, cleansing cream, cleansing foam, cleansing water, facial pack, spray or powder.

The cosmetically acceptable carrier contained in the present cosmetic composition, may be varied depending on the type of the formulation. For example, the formulation of ointment, pastes, creams or gels may comprise animal and vegetable fats, waxes, paraffins, starch, tragacanth, cellulose derivatives, polyethylene glycols, silicones, bentonite, silica, talc, zinc oxide or mixtures of these ingredients.

In the formulation of powder or spray, it may comprise lactose, talc, silica, aluminum hydroxide, calcium silicate, polyamide powder and mixtures of these ingredients. Spray may additionally comprise the customary propellants, for example, chlorofluorohydrocarbons, propane, butane, diethyl ether, or dimethyl ether.

The formulation of solution and emulsion may comprise solvent, solubilizer and emulsifier, for example water, ethanol, isopropanol, ethyl carbonate, ethyl acetate, benzyl alcohol, benzyl benzoate, propylene glycol, 1,3-butyleneglycol, oils, in particular cottonseed oil, groundnut oil, maize germ oil, olive oil, castor oil and sesame seed oil, glycerol fatty esters, polyethylene glycol and fatty acid esters of sorbitan or mixtures of these ingredients.

The formulation of suspension may comprise liquid diluents, for example water, ethanol or propylene glycol, suspending agents, for example ethoxylated isostearyl alcohols, polyoxyethylene sorbitol esters and polyoxyethylene sorbitan esters, microcrystalline cellulose, aluminum metahydroxide, bentonite, agar and tragacanth or mixtures of these ingredients.

The formulation of cleansing compositions with surfactant may comprise aliphatic alcohol sulfate, aliphatic alcohol ether sulfate, sulfosucinnate monoester, isethionate, imidazolium derivatives, methyl taurate, sarcosinate, fatty acid amide ether sulfate, alkyl amido betaine, aliphatic alcohol, fatty acid glyceride, fatty acid diethanolamide, vegetable oil, lanoline derivatives, ethoxylated glycerol fatty acid ester or mixtures of these ingredients.

Additional antioxidant ingredients and compositions can be selected from, but not limited to, Ascorbic acid, Ascorbic acid derivatives, Glucosamine ascorbate, Arginine ascorbate, Lysine ascorbate, Glutathione ascorbate, Nicotinamide ascorbate, Niacin ascorbate, Allantoin ascorbate, Creatine ascorbate, Creatinine ascorbate, Chondroitin ascorbate, Chitosan ascorbate, DNA Ascorbate, Carnosine ascorbate, Vitamin E, various Vitamin E derivatives, Tocotrienol, Rutin, Quercetin, Hesperedin (*Citrus sinensis*), Diosmin (*Citrus sinensis*), Mangiferin (*Mangifera indica*), Mangostin (*Garcinia mangostana*), Cyanidin (*Vaccinium myrtillus*), Astaxanthin (*Haematococcus algae*), Lutein (*Tagetes patula*), Lycopene (*Lycopersicum esculentum*), Resveratrol (*Polygonum cuspidatum*), Tetrahydrocurcumin (*Curcuma longa*), Rosmarinic acid (*Rosmarinus officinalis*), Hypericin (*Hypericum perforatum*), Ellagic acid (*Punica granatum*), Chlorogenic acid (*Vaccinium vulgaris*), Oleuropein (*Olea europaea*), α-Lipoic acid, Niacinamide lipoate, Glutathione, Andrographolide (*Andrographis paniculata*), Carnosine, Niacinamide, Potentilla erecta extract, Polyphenols, Grapeseed extract, Pycnogenol (Pine Bark extract), Pyridoxine, Magnolol, Honokiol, Paeonol, Resacetophenone, Quinacetophenone, arbutin, kojic acid, and combinations thereof.

The blood micro-circulation improvement ingredients and compositions can be selected from, but not limited to, Horse Chestnut Extract (*Aesculus hippocastanum* extract)), Esculin, Escin, Yohimbine, *Capsicum* Oleoresin, Capsaicin, Niacin, Niacin Esters, Methyl Nicotinate, Benzyl Nicotinate, Ruscogenins (Butchers Broom extract; *Ruscus aculeatus* extract), Diosgenin (*Trigonella foenumgraecum*, Fenugreek), Emblica extract (*Phyllanthus emblica* extract), Asiaticoside (*Centella asiatica* extract), *Boswellia* Extract (*Boswellia serrata*), Ginger Root Extract (*Zingiber Officianalis*), Piperine, Vitamin K, Melilot (*Melilotus officinalis* extract), Glycyrrhetinic acid, Ursolic acid, Sericoside (*Terminalia sericea* extract), Darutoside (*Siegesbeckia orientalis* extract), Amni visnaga extract, extract of Red Vine (*Vitis Vinifera*) leaves, apigenin, phytosan, luteolin, and combinations thereof.

The anti-inflammatory ingredients or compositions can be selected from, but not limited to, at least one antioxidant class of Cyclo-oxygenase (for example, COX-1 or COX-2) or Lipoxygenase (for example, LOX-5) enzyme inhibitors such as Ascorbic acid, Ascorbic acid derivatives, Vitamin E, Vitamin E derivatives, Tocotrienol, Rutin, Quercetin, Hesperedin (*Citrus sinensis*), Diosmin (*Citrus sinensis*), Mangiferin (*Mangifera indica*), Mangostin (*Garcinia mangostana*), Cyanidin (*Vaccinium myrtillus*), Astaxanthin (*Haematococcus algae*), Lutein (*Tagetes patula*), Lycopene (*Lycopersicum esculentum*), Resveratrol (*Polygonum cuspidatum*), Tetrahydrocurcumin (*Curcuma longa*), Rosmarinic acid (*Rosmarinus officinalis*), Hypericin (*Hypericum perforatum*), Ellagic acid (*Punica granatum*), Chlorogenic acid (*Vaccinium vulgaris*), Oleuropein (*Olea europaea*), alpha-Lipoic acid, Glutathione, Andrographolide, Grapeseed extract, Green Tea Extract, Polyphenols, Pycnogenol (Pine Bark extract), White Tea extract, Black Tea extract, (*Andrographis paniculata*), Carnosine, Niacinamide, and Emblica extract. Anti-inflammatory composition can additionally be selected from, but not limited to, Horse Chestnut Extract (*Aesculus hippocastanum* extract)), Esculin, Escin, Yohimbine, *Capsicum* Oleoresin, Capsaicin, Niacin, Niacin Esters, Methyl Nicotinate, Benzyl Nicotinate, Ruscogenins (Butchers Broom extract; *Ruscus aculeatus* extract), Diosgenin (*Trigonella foenumgraecum*, Fenugreek), Emblica extract (*Phyllanthus emblica* extract), Asiaticoside (*Centella asiatica* extract), *Boswellia* Extract (*Boswellia serrata*), Sericoside, Visnadine, Thiocolchicoside, Grapeseed Extract, Ginger Root Extract (*Zingiber Officinalis*), Piperine, Vitamin K, *Melilot* (*Melilotus officinalis* extract), Glycyrrhetinic acid, Ursolic acid, Sericoside (*Terminalia sericea* extract), Darutoside (*Siegesbeckia orientalis* extract), Amni visnaga extract, extract of Red Vine (*Vitis-Vinifera*) leaves, apigenin, phytosan, luteolin, and combinations thereof.

Certain divalent and polyvalent metal ions can also be present in the compositions of the present invention. The examples of such metal ions include zinc, copper, manganese, vanadium, chromium, cobalt, and iron.

EXAMPLES

All quantities are in weight percent amounts. The examples do not limit the scope of the present invention.

Example 1

Preparation of
N-[(2,4-Dihydroxyphenyl)ethylidene]glycine in water solution

Ingredients. (1) Water 97.5 (2) Resacetophenone 1.5 (3) Glycine 1.0. Procedure. The mixture of all ingredients is heated at 90 to 95 C for 2 hours. A solution of N-[(2,4-Dihydroxyphenyl)ethylidene]glycine in water is obtained.

Example 2

Preparation of
N-[(2,4-Dihydroxyphenyl)ethylidene]glycine Sodium in water solution Ingredients. (1) Water 96.91 (2) Sodium Bicarbonate 0.84 (3) Glycine 0.75 (4) Resacetophenone 1.5. Procedure. Mix (1) to (3). A clear solution is obtained. Heat to 80 to 90 C. Add (4). An instantaneous reaction occurs and a clear yellow solution is obtained. The mixing and heating is continued for 1 hour. A solution of N-[(2,4-Dihydroxyphenyl)ethylidene] glycine Sodium in water is thus obtained, yellow in color, pH 8.5.

Example 3

Preparation of
N-[(2,4-Dihydroxyphenyl)ethylidene]glycine from N-[(2,4-Dihydroxyphenyl)ethylidene]glycine Sodium in water solution Ingredients. (1) Water 96.91 (2) Sodium Bicarbonate 0.84 (3) Glycine 0.75 (4) Resacetophenone 1.5. Procedure. Mix (1) to (3). Heat to 70 to 80 C. Add (4). An instantaneous reaction occurs and a clear solution is obtained. The mixing and heating is continued for 1 hour. A solution of N-[(2,4-Dihydroxyphenyl)ethylidene]glycine Sodium in water is thus obtained, pH 8.5. Water is evaporated to ⅓ in volume and the solution allowed to cool. The pH is adjusted to 6.5 with citric acid (2.0 grams of 50% solution). N-[(2,4-Dihydroxyphenyl) ethylidene]glycine is obtained as an off-white to pale, yellow crystalline solid. Ir (ethanol cast film) 1600, 1509, 1443, 1378, 1322, 1272, 1173, 1137, 1062, 980, 769 cm-1.

Example 4

Preparation of
N-[(2,4-Dihydroxyphenyl)ethylidene]phenylalanine

Ingredients. (1) Water 95.8 (2) Sodium Bicarbonate 0.9 (3) Phenylalanine.H2O 1.8 (4) Resacetophenone 1.5. Procedure. Mix (1) to (3). Heat to 70 to 80 C. Add (4). An instantaneous reaction occurs and a clear yellow solution is obtained. The mixing and heating is continued for 1 hour. A solution of N-[(2,4-Dihydroxyphenyl)ethylidene]phenylalanine Sodium in water is thus obtained, pH 8.5. Water is evaporated to ⅓ in volume and the solution allowed to cool. The pH is adjusted to 6.5 with citric acid (2.0 grams of 50% solution). N-[(2,4-Dihydroxyphenyl)ethylidene]phenylalanine is obtained as an off-white to pale, yellow crystalline solid. Ir (ethanol cast film) 1596, 1505, 1440, 1372, 1324, 1265, 1177, 1140, 1096, 811, 704 cm-1.

Example 5

Preparation of
N-[(2,4-Dihydroxyphenyl)ethylidene]arginine

Ingredients. (1) Water 95.5 (2) Sodium Bicarbonate 0.9 (3) Arginine.2H2O 2.1 (4) Resacetophenone 1.5. Procedure. Mix (1) to (3). Heat to 70 to 80 C. Add (4). An instantaneous reaction occurs and a clear yellow solution is obtained. The mixing and heating is continued for 1 hour. A solution of N-[(2,4-Dihydroxyphenyl)ethylidene]arginine Sodium in water is thus obtained, pH 9.5. Water is evaporated to ⅓ in volume and the solution allowed to cool. The pH is adjusted to 6.5 with citric acid (2.0 grams of 50% solution). N-[(2,4-Dihydroxyphenyl)ethylidene]arginine is obtained as an off-white to pale, yellow crystalline solid. Ir (ethanol cast film) 1601, 1507, 1443, 1381, 1271, 1174, 1138, 1100, 981, 870, 769 cm-1.

Example 6

Preparation of
N-[(2,4-Dihydroxyphenyl)ethylidene]cysteine

Ingredients. (1) Water 97.3 (2) Sodium Bicarbonate 0.9 (3) L-Cysteine 1.2 (4) Resacetophenone 1.5. Procedure. Mix (1) to (3). Heat to 70 to 80 C. Add (4). An instantaneous reaction occurs and a clear yellow solution is obtained. The mixing and heating is continued for 1 hour. A solution of N-[(2,4-Dihydroxyphenyl)ethylidene]cysteine Sodium in water is thus obtained, pH 8.5. Water is evaporated to ⅓ in volume and the solution allowed to cool. The pH is adjusted to 6.5 with citric acid (2.0 grams of 50% solution). N-[(2,4-Dihydroxyphenyl)ethylidene]cysteine is obtained as a pale, yellow crystalline solid. Ir (Ethanol cast film) 1630, 1603, 1509, 1450, 1380, 1321, 1272, 1175, 1140, 1063, 771 cm-1.

Example 7

Preparation of
N-[(2,4-Dihydroxyphenyl)ethylidene]glycine copper
complex [FIG. 2, Structure B, M=Cu, R=4-Hydroxy,
R"=H] in Water-Alcohol medium Ingredients. (1) Water 66.18 (2) Ethanol 30.0 (3) Resacetophenone 1.5 (4) Copper Bis-glycinate Hydrate 2.32. Procedure. The mixture of all ingredients is heated at 80 to 85 C for 2 hours. The color changes from blue to bluish green, and a green precipitate is formed. The precipitate is filtered and washed with water to remove any unreacted copper glycinate, then washed with ethanol to remove any unreacted Resacetophenone. Infra-red (ir) spectrum shows strong bands at 1606, 1570, 1525, and 1136 cm-1. It is possibly solvated with ethanol.

Example 8

Preparation of
N-[(2,4-Dihydroxyphenyl)ethylidene]glycine copper
complex in water medium Ingredients. (1) Water 96.18 (2) Resacetophenone 1.5 (3) Copper Bis-glycinate Hydrate 2.32. Procedure. The mixture of all ingredients is heated at 90 to 95 C for 2 hours. The color changes from blue to bluish green, and a greenish blue precipitate is formed. The precipitate is filtered and washed with water to remove any unreacted copper glycinate, then washed with ethanol to remove any unreacted Resacetophenone. A bluish green solid is obtained. Infra-red (ir) spectrum (ethanol cast film) shows strong bands at 1605, 1579, 1386, 1240, 1206, 1059, 860, 792 and 743 cm-1. Copper Glycinate, for comparison, has strong Ir bands at 1610, 1367, 1330, 1139, 1048, 742, and 647 cm-1.

Example 9

Preparation of
N-[(2,4-Dihydroxyphenyl)ethylidene]glycine Zinc in
water medium

Ingredients. (1) Water 96.20 (2) Resacetophenone 1.5 (3) Zinc Bis-glycinate Hydrate 2.30. Procedure. The mixture of all ingredients is heated at 90 to 95 C for 2 hours. Water is then evaporated to ½ the volume, mixture cooled to room temperature, and iso-propanol (100 ml) is added with mixing and cooling. The precipitate is filtered and washed with water to remove any unreacted zinc glycinate, then washed with iso-propanol to remove any unreacted Resacetophenone. A white solid is obtained. Infra-red (ir) spectrum (ethanol cast film) shows strong bands at 2871, 1624, 1456, 1370, 1329, 1252, 1096, 947, 844, and 813 cm-1. Zinc Glycinate, for comparison, has strong Ir bands at 2979, 1573, 1559, 1399, 1317, 1046, and 909 cm-1. Resacetophenone, for comparison, has ir bands at 1593, 1499, 1439, 1373, 1267, 1169, 1063, 979, 869, 765, 703 cm-1.

Example 10

Preparation of
N-[(2,4-Dihydroxyphenyl)ethylidene]glycine Zinc in
water/PEG-6 medium Ingredients. (1) Water 46.20 (2) Resacetophenone 1.5 (3) Zinc Bis-glycinate Hydrate 2.30 (4) PEG-6 50.0. Procedure. The mixture of (1) and (3) is heated at 90 to 95 C till a clear solution is formed. The mixture of (2) and (4) is then heated at 50 to 60 C to a clear solution. This is added to zinc glycinate solution with mixing and heating continued at 90 to 95 C for 2 hours, then cooled to room temperature. The white crystalline precipitate thus formed is filtered and washed with water to remove any unreacted copper glycinate, then washed with iso-propanol to remove any unreacted Resacetophenone. A white solid is obtained. Infra-red (ir) spectrum (ethanol cast film) shows strong bands at 2871, 1624, 1456, 1370, 1329, 1252, 1096, 947, 844, and 813 cm-1.

Example 11

Preparation of
N-[(2,4-Dihydroxyphenyl)ethylidene]glycine
Manganese in water medium Ingredients. (1) Water 96.40 (2) Resacetophenone 1.5 (3) Manganese Bis-glycinate 2.10. Procedure. The mixture of all ingredients is heated at 90 to 95 C for 2 hours. Water is then evaporated off to ½ of its original volume. Ethanol (50 mL) is then added and the mixture cooled. A purplish crystalline material is formed. The precipitate is filtered and washed with water to remove any unreacted zinc glycinate, then washed with iso-propanol to remove any unreacted Resacetophenone. A purplish brown crystalline material is obtained. Infra-red (ir) spectrum (ethanol cast film) shows strong bands at 2896, 1599, 1507, 1408, 1330, 1280, 1134, 908, 700 cm-1.

Example 12

Preparation of
N-[(2,4-Dihydroxyphenyl)ethylidene]histidine
Chromium Histidinate Complex [FIG. 2, Structure
C, R=4-Hydroxy, R"=methyl-(4-imidazolyl), M=Cr]

Ingredients. (1) Water 92.80 (2) Resacetophenone 1.5 (3) Chromium tris-histidinate 5.7. Procedure. The mixture of all ingredients is heated at 90 to 95 C for 2 hours. Water is then evaporated off to ⅓ of its original volume. Ethanol (50 mL) is then added and the mixture cooled. A red solution is formed. Infra-red (ir) spectrum (ethanol cast film) shows strong bands at 1603, 1509, 1442, 1374, 325, 1268, 1142, 1070, 988, 804 cm-1.

Example 13

Preparation of
N-[(2,4-Dihydroxyphenyl)ethylidene]glycine Iron in
water medium

Ingredients. (1) Water 96.50 (2) Resacetophenone 1.5 (3) Iron Bis-glycinate 2.0. Procedure. The mixture of all ingredients is heated at 90 to 95 C for 2 hours. The green color of iron glycinate changes to a dark red-brown color. Water is then evaporated off to ½ of its original volume. Ethanol (50 mL) is then added and the mixture cooled. A reddish brown material is formed. The precipitate is filtered and washed with water to remove any unreacted iron glycinate, then washed with ethanol to remove any unreacted Resacetophenone. A reddish brown crystalline material is obtained. Infra-red (ir) spectrum (ethanol cast film) shows strong bands at 3173, 1635, 1605, 1515, 1450, 1381, 1329, 1279, 1178, 1144, 1064, 772 cm-1. Iron Bis-glycinate, for comparison, has major ir band at 1557, 1515, 1390, 1317, 1110, 1035, 901 cm-1.

Example 14

Preparation of Resacetophenone Copper Complex in Water Medium

Ingredients. (1) Water 94.68 (2) Resacetophenone 3.0 (3) Copper Bis-glycinate Hydrate 2.32. Procedure. The mixture of all ingredients is heated at 90 to 95 C for 2 hours. The color changes from blue to bluish green, and a greenish blue precipitate is formed. The precipitate is filtered and washed with water to remove any unreacted copper glycinate, then washed with ethanol to remove any unreacted Resacetophenone. A greenish blue solid is obtained. Infra-red (ir) spectrum (ethanol cast film) shows strong bands at 1591, 1386, 1329, 110, 1060, 913, 742, and 693 cm-1. In comparison, Resacetophenone shows strong ir bands at 1625, 1593, and 1268 cm-1.

Example 15

Skin Whitening and Anti-Wrinkle Serum

Ingredients. (1) Ethyl Lactate 20.0 (2) Polyalkyleneoxy Polyamide 0.5 (3) N-[(2,4-Dihydroxyphenyl)ethylidene]glycine (from Example 1) 5.0 (4) PEG-6 70.0 (5) Arbutin 4.0 (6) Preservatives 0.5. Procedure. Make serum base by mixing (1) to (3) at room temperature or slight heating. Pre-mix (4) to (6) to a clear solution and add to main batch with mixing. The product has light green serum like appearance.

Example 16

Anti-Acne and Facial Oil Control Cream

Ingredients. (1) Deionized water 79.5 (2) Cetearyl alcohol (and) dicetyl phosphate (and) Ceteth-10 phosphate 5.0 (3) Cetyl alcohol 2.0 (4) Glyceryl stearate (and) PEG-100 stearate 4.0 (5) Ethyl Lactate 5.0 (6) N-[(2,4-Dihydroxyphenyl)ethylidene]glycine molybdenum complex 3.0 (7) Paeonol 1.0 (8) Preservatives 0.5. Procedure. Mix 1 to 5 and heat to 75-80° C. Adjust pH to 4.0 4.5. Cool to 35-40 C with mixing. Add 6 to 8 with mixing. Adjust pH to 4.0-4.5, if necessary. An off-white cream is obtained.

Example 17

Skin Discoloration and Age Spots Cream

Via In-Situ Generated
N-[(2,4-Dihydroxyphenyl)ethylidene]glycine

Ingredients. (1) Water 53.9 (2) Dicetyl Phosphate (and) Ceteth-10 Phosphate 5.0 (3) Glyceryl Stearate (and) PEG-100 Stearate 4.0 (4) Phenoxyethanol 0.7 (5) Chlorphenesin 0.3 (60) Titanium Dioxide 0.2 (7) Sodium Hydroxide 0.5 (8) Magnolol 0.2 (9) *Boswellia Serrata* 0.5 (10) Cetyl Dimethicone 1.5 (11) Tetrahydrocurcuminoids 0.5 (12) Shea butter 2.0 (13) Ximenia oil 1.0 (14) Water 5.0 (15) Niacinamide Lactate 1.0 (16) Niacinamide Hydroxycitrate 3.1 (17) 2,4-Dihydroxyacetophenone 1.5 and Glycine 1.0 (for in-situ generation of N-[(2,4-Dihydroxyphenyl)ethylidene]glycine) (18) Paeonol 1.5 (19) Carnosine 0.1 (20) Cyclomethicone, Dimethicone Crosspolymer 2.0 (21) Arbutin 0.5 (22) Polysorbate-20 2.0 (23) Ethyl Lactate 12.0. Procedure. Mix (1) to (13) and heat at 70 to 80 C till homogenous. Cool to 40 to 50 C. Premix (14) to (16) and add to batch with mixing. Mix (17) to (23) to a clear solution and add to main batch mix. Cool to room temperature. An off-white cream is obtained.

Example 18

MMP Inhibitor Acne Cream

Ingredients. (1) Water 53.9 (2) Dicetyl Phosphate (and) Ceteth-10 Phosphate 5.0 (3) Glyceryl Stearate (and) PEG-100 Stearate 4.0 (4) Phenoxyethanol 0.7 (5) Chlorphenesin 0.3 (60) Titanium Dioxide 0.2 (7) Sodium Hydroxide 0.5 (8) Magnolol 0.2 (9) *Boswellia Serrata* 0.5 (10) Cetyl Dimethicone 1.5 (11) Tetrahydrocurcuminoids 0.5 (12) Shea butter 2.0 (13) Ximenia oil 1.0 (14) Niacinamide Hydroxycitrate 2.2 (15) Ethyl Lactate 15.0 (16) Niacinamide Salicylate 4.0 (17) N-[(2,4-Dihydroxyphenyl)ethylidene]arginine molybdenum complex 1.1 (18) Paeonol 1.5 (19) Carnosine 0.1 (20) Cyclomethicone, Dimethicone Crosspolymer 2.0 (21) Arbutin 0.5 (22) Salicylic Acid 2.0 (23) Polysorbate-20 2.0 (24) Polyacrylamide 2.0. Procedure. Mix (1) to (15) and heat at 70 to 80 C till homogenous. Cool to 40 to 50 C. Premix (16) to (23) and heat, if necessary, to a solution and add to main batch with mixing. Cool to room temperature and add (24) and mix. An off-white cream is obtained.

Example 19

MMP Inhibitor Skin Brightening Cleanser

Ingredients. (1) PEG-6 47.229 (2) Hydroxypropyl Guar 0.4 (3) Sodium Cocoyl Isethionate 20.0 (4) Sodium Lauryl Sulfoacetate 5.0 (5) *Boswellia Serrata* 0.05 (6) L-Glutathione 0.01 (7) Resveratrol 0.01 (8) N-[(2,4-Dihydroxyphenyl)ethylidene]glycine 1.1 (9) 2,6-Dihydroxy Acetophenone 0.001 (10) Ascorbic acid 10.0 (11) Phenoxyethanol 0.7 (12) Ethylhexylglycerin 0.3 (13) Fragrance 0.2 (14) Ethylhexyl Lactate 15.0. Procedure. Mix (1) and (2) to a clear thin gel. Add (3) and (4) and mix. Premix (5) to (14) to a solution. Add to main batch and mix. A white cream-like cleanser is obtained.

Example 20

Anti-Inflammatory MMP Inhibitor Transparent Gel

Ingredients. (1) Ethyl Lactate 96.75 (2) Hydroxypropyl Guar 1.0 (3) Ximenia Oil 0.1 (4) Capsaicin 0.25 (5) Magnolol (and) Honokiol 0.2 (6) Paeonol 0.5 (7) N-[(2,4-Dihydroxyphenyl)ethylidene]glycine copper complex 0.2 (8) Fragrance 1.0. Procedure. Mix (1) and (2) and heat at 50 to 60 C till clear. Cool to 40 to 45 C and add all other ingredients and mix. Cool to room temperature. A transparent gel-like product is obtained.

Example 21

Hair Growth Promoting Shampoo

Ingredients. (1) Water 64.2 (2) N-[(2,4-Dihydroxyphenyl) ethylidene]glycine 1.2 (3) Sodium Lauryl Sulfoacetate 10.0 (4) Disodium Laureth Sulfosuccinate 20.0 (5) Phenoxyethanol 0.7 (6) Chlorphenesin 0.3 (7) PEG-120 Methyl Glucose Dioleate 2.5. (8) Hydrolyzed Soy Protein 0.5 (9) Hydrolyzed Silk Protein 0.5 (10) Oat Extract 0.1. Procedure. Mix (1) to (7) and heat at 60 to 70 C to a clear solution. Cool to 35 to 40 C and add all other ingredients and mix. Cool to room temperature.

Example 22

Heat Releasing Face and Body Skin Brightening Cleanser

Ingredients. (1) Ethyl Lactate 5.0 (2) Hydroxypropyl Guar 0.4 (3) PEG-6 36.9 (4) Glycerin 2.0 (5) Vitamin E 0.1 (6) Botanicals blend 0.1 (7) Zeolite 30.0 (8) Disodium Lauryl Sulfosuccinate powder 7.5 (9) Sodium Cocoyl Isethionate powder 11.0 (10) Shea butter 1.1 (11) Apricot Kernel Oil 0.5 (12) N-[(2,4-Dihydroxyphenyl)ethylidene]glycine copper complex 1.1 (13) Mango butter 0.5 (14) Fragrance 3.0 (15) Preservative 0.8. Procedure. Mix (1) to (3) and heat at 40 to 50 C till a clear gel is obtained (about one hour). Pre-mix (4) to (6) and add to main batch and mix. Add (7) to (13) and mix. Cool to 35 to 45 C. Add all other ingredients to main batch and mix. Cool to room temperature to an off-white paste. Upon application to slightly wet face or body, heat release is experienced and voluminous foam is generated upon rubbing skin with some more water.

Example 23

Facial Glow Serum with In-Situ Generated N-{1-[(2-beta-D-Glucopyranosyloxy)-4,6-dihydroxyphenyl)-]-3-(4-hydroxyphenyl)-1-propylidene}glycine, derived from Phloridzin and Glycine Ingredients. (1) Butylene Glycol 57.9 (2) Water 10.0 (3) Ascorbic Acid 10.0 (4) Diglycerol 10.0 (5) Bis-PEG-18 Methyl Ether Dimethyl Silane 4.0 (6) Acrylates/Aminoacrylates/C-10-30 Alkyl PEG-20 Itaconate Copolymer 4.0 (7) Phloridzin 1.5 (8) Glycine 1.0 (9) Magnolol 0.2 (10) Baicalin 0.2 (11) Coleus Forskohlii Root Extract 0.1 (12) Preservative 1.0. Procedure. Make Premix A by mixing (2), (7), and (8) at 60 to 70 C for 30 min., then add (3) with mixing. Make Premix B by mixing all other ingredients, except (6), separately. Mix Premix A and Premix B, then add (6) with mixing to adjust viscosity.

Example 24

Facial Glow Cream with In-Situ Generated N-[(2,4-Dihydroxyphenyl)ethylidene]Glycine Sodium Complex Ingredients. (1) Water 72.45 (2) Dicetyl phosphate and Ceteth-10 phosphate 5.0 (3) Glyceryl Stearate and PEG-100 stearate 4.0 (4) Diglycerol 2.0 (5) Shea butter 2.0 (6) 2,4-Dihydroxyacetophenone 1.5 (7) Sodium glycinate 2.2 (8) Capuacu butter 1.0 (9) Sodium hydroxide 0.25 (10) *Boswellia serrata* extract 0.5 (11) Tetrahydrocurcumin 0.2 (12) Paeonol 0.2 (13) Arbutin 1.1 (14) Coleus Forskohlii Root extract 0.1 (15) Polysorbate-20 4.0 (16) Carnosine 0.1 (17) Preservative 1.0 (18) Polyacrylamide and C13-14 Isoparaffin and Laureth-7 2.0. Procedure. Make Premix A by mixing (1), (6), and (7) at 80 to 90 C. Add all other ingredients and continue mixing until homogenous. Cool to room temperature.

Example 25

Facial Glow Cleanser with In-Situ Generated Triethanolammonium N-[(2,4-Dihydroxyphenyl)ethylidene]Glycinate Ingredients. (1) Water 52.0 (2) 2,4-Dihydroxyacetophenone 1.5 (3) Triethanolammonium Glycinate 1.5 (4) Arbutin 0.5 (5) Magnolol 0.2 (6) Coleus Forskohlii Root Extract 0.3 (7) Preservative 1.0 (8) Glycerin 1.0 (9) Sodium Methyl Cocoyl Taurate 20.0 (10) Sodium Cocoyl Isethionate 20.0 (11) PEG-120 Methyl Glucose Dioleate 2.0. Procedure. Mix (1) to (3) at 80 to 90 C. Add all other ingredients. Continue mixing until homogenous. Cool to room temperature.

Example 26

Facial Glow Cleanser with In-Situ Generated N-[(2,4-Dihydroxyphenyl)ethylidene]Glycine Zinc Complex Ingredients. (1) Water 51.4 (2) 2,4-Dihydroxyacetophenone 1.5 (3) Zinc Bis-Glycinate 2.1 (4) Arbutin 0.5 (5) Magnolol 0.2 (6) Coleus Forskohlii Root Extract 0.3 (7) Preservative 1.0 (8) Glycerin 1.0 (9) Sodium Methyl Cocoyl Taurate 20.0 (10) Sodium Cocoyl Isethionate 20.0 (11) PEG-120 Methyl Glucose Dioleate 2.0. Procedure. Mix (1) to (11) at 80 to 90 C. Continue mixing until homogenous. Cool to room temperature.

Example 27

"Molybdenum Cofactor" Acne Cream

Ingredients. (1) Water 53.9 (2) Dicetyl Phosphate (and) Ceteth-10 Phosphate 5.0 (3) Glyceryl Stearate (and) PEG-100 Stearate 4.0 (4) Phenoxyethanol 0.7 (5) Chlorphenesin 0.3 (60) Titanium Dioxide 0.2 (7) Sodium Hydroxide 0.5 (8) Magnolol 0.2 (9) *Boswellia Serrata* 0.5 (10) Cetyl Dimethicone 1.5 (11) Tetrahydrocurcuminoids 0.5 (12) Shea butter 2.0 (13) Ximenia oil 1.0 (14) Niacinamide Hydroxycitrate 2.2 (15) Ethyl Lactate 15.0 (16) Niacinamide Salicylate 4.0 (17) N-[(2-Hydroxyphenyl)ethylidene]glycine molybdenum complex 1.1 (18) Paeonol 1.5 (19) Carnosine 0.1 (20) Cyclomethicone, Dimethicone Crosspolymer 2.0 (21) Arbutin 0.5 (22) Salicylic Acid 2.0 (23) Polysorbate-20 2.0 (24) Polyacrylamide 2.0. Procedure. Mix (1) to (15) and heat at 70 to 80 C till homogenous. Cool to 40 to 50 C. Premix (16) to (23) and heat, if necessary, to a solution and add to main batch with mixing. Cool to room temperature and add (24) and mix. An off-white cream is obtained.

In-Vitro and Human Clinical Testing Results.

These tests were conducted to establish the treatment of the groups of the following topical conditions that relate to malfunction of enzyme(s) related to said group of topical conditions:

(i) Darkened skin including age spots, circles around eyes and stretch marks,
(ii) Acne,
(iii) Premature hair aging including hair loss and graying,
(iv) Inflammation including intra-cellular and extra-cellular inflammation,
(v) Skin aging including wrinkles and fine lines,
(vi) Loss of collagen including thinning skin and loss of skin pliability,
(vii) Malfunction of tyrosinase group of enzymes (via inhibition of tyrosinase group of enzymes),
(viii) Malfunction of matrix metalloprotease group of enzymes (via inhibition of matrix metalloprotease group of enzymes).

The method of treatment of darkened skin including age spots, circles around eyes and stretch marks of the present invention relates to the inhibition of both tyrosinase and MMP group of enzymes, as it is the skin colorant melanin that is responsible for those skin conditions. Any agent that would cause a treatment of said conditions shall also be considered to provide the end benefit of that treatment, i.e., a skin whitening agent for dark skin, age spots, and dark circles around the eyes. It is usually all of the above skin conditions that accompany.

Similarly, premature hair aging including hair loss and graying is caused by a combination of two malfunctioning enzymes, i.e., tyrosinase and MMP. The tyrosinase causes the melanin color change, while MMP causes the inflammation of hair root zone that results in premature hair loss. The treatment of this malfunction by the method of the present invention causes the retardation of premature hair loss and hair graying.

Inflammation including intra-cellular and extra-cellular inflammation is mainly caused by up-regulated MMP group of enzymes, the treatment of which causes an anti-inflammatory affect.

Up-regulated MMP enzymes, and down-regulated superoxide dismutases cause skin aging including wrinkles and fine lines; the treatment of which by the method of the present invention causes the retardation of skin aging including wrinkles and fine lines.

Up-regulated MMP enzymes and reduction of antioxidant efficacy of cellular enzymes including superoxide dismutases cause the loss of collagen including thinning skin and loss of skin pliability; the treatment of which by the method of the present invention causes the enhancement of collagen, which concomitantly causes an increase both in the thickness of skin and its pliability.

Thus, it is clear to understand that the method of the present invention, which causes the correction of the functioning of both tyrosinase and MMP GROUP of enzymes, can provide a surprising and unexpected array of treatments for various skin conditions classified into groups of inter-related disorders, as discussed above. This is worthy of note that the method of the treatment of the present invention provides a treatment for a group of inter-related skin conditions, and not just one or two of said conditions.

Inhibition of Matrix Metalloprotease and Tyrosinase Group of Enzymes.

Method. N-[(2,4-Dihydroxyphenyl)ethylidene]glycine zinc and N-[(2,5-Dihydroxyphenyl)ethylidene]glycine zinc show some structural similarity to hydroquinone. Both samples have already been evaluated for anti-tyrosinase activity and N-[(2,4-Dihydroxyphenyl)ethylidene]glycine zinc showed tyrosinase inhibition. We now also show that both molecules show MMP inhibition activity with N-[(2,4-Dihydroxyphenyl)ethylidene]glycine zinc being the most potent one.

In vitro specific inhibition of MMP-2 and MMP-9 activity by 2,4-dihydroxyacetophenone and 2,5-dihydroxyacetophenone was estimated with assay kits from Biomol Corporation. Recombinant human MMP-1 enzyme was obtained from R&D Systems. The enzyme was first activated with APMA according to the protocol provided by R&D Systems. The experimental conditions for the screening of MMP-1 inhibitors were similar to the settings used for MMP-2 and MMP-9 testing.

Results are summarised below. N-[(2,4-Dihydroxyphenyl) ethylidene]glycine zinc showed very good and general inhibition of Matrix metalloproteases under these experimental conditions whereas the anti-MMP activity of N-[(2,5-Dihydroxyphenyl)ethylidene]glycine zinc seemed to be weaker, but still quite acceptable.

In vitro inhibition of MMP1, 2 and 9 for several samples (mcg=micro-grams).

| Compound | 50% Inhibition Concentration | | |
| --- | --- | --- | --- |
| | MMP-1 | MMP-2 | MMP-9 |
| N-[(2,4-Dihydroxyphenyl)ethylidene]glycine zinc | 15 mcg/mL | 13 mcg/mL | 17 mcg/mL |
| N-[(2,5-Dihydroxyphenyl)ethylidene]glycine zinc | 89 mcg/Ml | 84 mcg/mL | 110 mcg/mL |

Inhibition of Tyrosinase Group of Enzymes.
Method. Kinetic analysis of 2,4 DHA inhibition.

All reactions were performed at 20 C, in phosphate buffer 100 mM, pH 6.8, mushroom tyrosinase.

| Compound | Tyrosinase Inhibitory Concentration |
| --- | --- |
| N-[(2,4-Dihydroxyphenyl)ethylidene]glycine zinc | 3.3 milli-molar |
| N-[(2,5-Dihydroxyphenyl)ethylidene]glycine zinc | >100 milli-molar |
| Arbutin (control) | 25 milli-molar |

These results show that N-[(2,4-Dihydroxyphenyl)ethylidene]glycine zinc (from Resacetophenone and zinc glycinate) is an excellent inhibitor of tyrosinase group of enzymes.

Clinical Testing for the Treatment of Skin Condition.
Test Samples.

Example 27

Serum A

Ingredients. (1) Water 10.0 (2) Ascorbic Acid 10.0 (3) Butylene Glycol 58.0 (4) Diglycerol 10.0 (5) N-[(2,4-Dihydroxyphenyl)ethylidene]glycine 3.0 (from Resacetophenone 2.5 and Zinc Glycinate 0.5) (6) Preservatives 1.0 (7) Dow Corning Cosmetic Wax 2501 4.0 (8) Structure Plus 4.0. Procedure. Ingredients 1 to 6 are mixed and heated at 60 to 65 Celsius (C) till a solution is obtained then cooled to 35 to 40 C and ingredient 7 and 8 are added with mixing to a desired viscosity. It is cooled to room temperature. A serum-like product is obtained, pH 3.5. It is marked Serum A in the clinical testing described herein.

Example 28

Serum B

A control sample, made as above for Serum A, but without any zinc glycinate and with proportionately increased amount of butylene glycol, was also prepared (pH 3.1) and labeled Serum B in the clinical testing described herein.

Clinical Testing I: Serum A Versus Placebo.

Ballistometry showed a decrease in skin stiffness at 1 week in the treated group, and an increase in the placebo group. The placebo group continues to increase in stiffness at one month. This study started in the late summer and as the season changes the temperature has dropped considerably and the humidity is lower. Typically we start to see the onset of drier skin as colder weather progresses. The amplitude measurement has a decrease in the placebo group, but the treated group had a slight increase. As skin ages, we generally see a decrease in the amplitude measurement.

Laser Doppler There was an increase in the microcirculation of the skin at the 1-week measurement in both the placebo and treated groups. There was no change at the 1-month measurement.

Silastic Castings These results are reported as % change in fine lines and wrinkles. The castings at 1 week and 1 month were compared to the baseline castings. The castings obtained from the treated group showed a greater decrease in fine lines and wrinkles.

|  |  | Fine Lines & Wrinkles | | |
|---|---|---|---|---|
|  |  | Increase | No Change | Decrease |
| PLACEBO | 1 Week | 60 | 30 | 10 |
|  | 1 Month | 70 | 23 | 7 |
| TREATED | 1 Week | 30 | 30 | 40 |
|  | 1 Month | 20 | 20 | 60 |

Photographic Assessment at 1 Month:
Photographs were evaluated for skin texture, pigmentation, pore-size, skin tone and clarity.
Treated- 8 of 15 subjects showed an overall improvement in their skin.
Placebo- 2 of 15 subjects showed an overall improvement in their skin.

Conclusions of Clinical Testing (I).

1. Comparison of the Treated Group Versus the Placebo Group Exhibited:
   Reduced breakouts (acne-type).
   Softer skin, smoother complexion (less wrinkles, more pliable).
   Skin looks and feels cleaner (less inflammation).
   Reduced pore-size.
   Reduced facial oil.

2. Subject's Assessment of their Skin:
   The subjects were asked to evaluate the skin care regimen that they were prescribed.
   Placebo—6 of 15 report a positive response to the prescribed skin care.
   Treated—14 out of 15 report a positive response to the prescribed skin care 3. Safety/Adverse Reactions:
   There were no reported incidences of skin irritation during this study. This establishes anti-inflammatory affect.
   Clinical Testing II: Serum A Versus Serum B Versus Placebo.
   The study was a double blinded, pilot, controlled, single center study. A total of 24 subjects participated in the study. They were divided into two groups of 12 subjects each. The test samples (with and without ascorbyl gluconate) were made as described in Example 2. Group-A, applied the Serum-A, while the Group-B applied the Serum-B. Each subject was asked to use the given test products on left under-eye for a period of 4 weeks. The right under-eye was the untreated eye. The subjects were assessed on 0 day, and at the end of the $1^{st}$, $2^{nd}$, $3^{rd}$ and the $4^{th}$ week. The assessment was carried out by a Dermatologist for the improvement in the (1) dark circles, (2) puffiness, and (3) wrinkles under the eye. Elastometer readings were taken for the crowfeet area to assess the improvement in skin elasticity.

2.1 Investigational Products.
      The investigational products were the two under eye serum formulations and were coded A and B as follows:
      Serum from Example 2: Serum-A (With ascorbyl gluconate).
      Serum Modified from Example 2: Serum-B (Only ascorbic acid, no ascorbyl gluconate).

2.2 Controls For The Study.
      The right under-eye was untreated and that was taken as the control untreated site.

2.3 Subject Population.
      Total 24 subjects were selected as per the inclusion and exclusion criteria.

2.4 Inclusion Criteria:
      i. Male and Female (30:70) subjects in generally good health.
      ii. Subjects in the age group of 25-45 years.
      iii. Subject has not participated in a similar investigation in the past four weeks.
      iv. Subjects have not used similar products for the last 4 weeks.
      v. Subjects willing to give a written informed consent and come for regular.
      vi. Follow-up.
      vii. Subjects should have an under eye puffiness score of 2-3, and under eye dark circle score of 2-3 as mentioned in section 9 of this protocol.

2.5 Exclusion Criteria
      i. A Known history or present condition of Allergic response to any cosmetic product.
      ii. Subject having skin disease (e.g. psoriasis, atomic dermatitis or other cutaneous manifestations), which would interfere with the test readings.
      iii. Subjects having melasma.
      iv. Subjects on medications (e.g. steroids or antihistamines), which would compromise the study.
      v. The subject is pregnant/nursing.

2.6 Duration of Study: Four Weeks.

3.0 Study Outline.

3.1 Product Application.
      The respective test sample was provided to the subjects after the baseline reading. The subjects applied approximately 0.5 grams of the test products on the left under-eye and evenly spread the product gently extending up to the crowfeet region with light strokes till absorbed into the skin. The right under-eye was considered as control or untreated site. The test sample was applied twice daily (i.e. once after bath and second before bedtime) for a period of four weeks on the left under eye region.

3.2 Clinical Measurements.

3.2.1 Visual Assessment of Under-eye (By Dermatologist).
      The dermatologist graded the both the under-eyes of the subjects on the baseline day and at the end of the $1^{st}$, $2^{nd}$, $3^{rd}$ and $4^{th}$ week as per the following criteria.
      (1) Dark circles—The dermatologist graded the under eye dark circles on both the left and right under-eye by using the following scale (half points used when necessary):

| Description | Score |
|---|---|
| No dark circles | 0 |
| Mild dark circles | 1 |
| Moderate dark circles | 2 |
| Severe dark circles | 3 |

(2) Puffiness—The dermatologist graded the under eye puffiness on both the left and right under-eye by using the following scale (half points used when necessary):

| Description | Score |
| --- | --- |
| No puffiness | 0 |
| Mild puffiness | 1 |
| Moderate puffiness | 2 |
| Severe puffiness | 3 |

(3) Wrinkles—The dermatologist graded the under eye wrinkles on both the left and right under-eye by using the following scale (half points used when necessary):

| Description | Score |
| --- | --- |
| No wrinkles | 0 |
| Very fine lines | 1 |
| Moderate wrinkles | 2 |
| Deep set wrinkles | 3 |

3.2.3 Instrumental Assessment.

Elastometer: Skin elasticity of both the crowfeet area was recorded using Elastometer.

4.0 Results and Statistical Analysis.

4.1 Dermatologist's Assessment.

4.1.1 Dark circles.

Serum-A. Compared to the baseline scores, there is a good improvement in the dark circle scores for the treated under-eye. The scores for the untreated under-eye also seem to improve albeit only to a small extent.

Serum-B. Compared to the baseline scores, there is a good improvement in the dark circle scores for the treated under-eye. The scores for the untreated under-eye also seem to improve albeit only to a small extent. However, the differences in improvement between untreated & treated under-eye scores are not statistically significant. 5 of the 12 subjects in the Serum-B group showed significant improvement in the reduction of dark circles.

Serum-A Compared to Serum-B. If the improvements in the scores for the treated under-eye over the improvements in the scores for the untreated under-eye are compared, there is no statistically significant difference between the improvement in dark circles due to Serum-A and Serum-B, although the stability of Serum A is better.

4.1.2 Puffiness.

Serum-A. Compared to the baseline scores, there is a good improvement in the puffiness scores for the treated under-eye. The scores for the untreated under-eye also seem to improve albeit only to a small extent.

Serum-B. Compared to the baseline scores, there is a good improvement in the puffiness scores for the treated under-eye. The scores for the untreated under-eye also seem to improve albeit only to a small extent.

Serum-A Compared to Serum-B. If the improvements in the scores for the treated under-eye over the improvements in the scores for the untreated under-eye are compared, there is no statistically significant difference between the improvement in puffiness due to Serum-A and Serum-B, although the stability of Serum A is better.

4.1.3 Wrinkles.

Serum-A. Compared to the baseline scores, there is a good improvement in the scores for wrinkles for the treated under-eye. The scores for the untreated under-eye also seem to improve albeit only to a small extent.

Serum-B. Compared to the baseline scores, there is a good improvement in the scores for wrinkles for the treated under-eye. The scores for the untreated under-eye also seem to improve albeit only to a small extent.

Serum-A Compared to Serum-B. If the improvements in the scores for the treated under-eye over the improvements in the scores for the untreated under-eye are compared, Serum-A shows better improvement in reduction of wrinkles post week-3, and the stability of Serum A is better.

4.2 Instrumental assessment of Crowfeet area: Elastometer.

Serum-A. Compared to the baseline scores, there is an improvement in the Elastometer readings scores for the treated crowfeet area. Eight of the 11 subjects show significant improvement in Elastometer readings for the treated crowfeet area.

Serum-B. Compared to the baseline scores, there is an improvement in the Elastometer readings scores for the treated crowfeet area. However, the extent of improvement is fluctuating over the four-week period.

Serum-A Compared to Serum-B. There is no statistically significant difference between Serum-A and Serum-B, although serum A is directionally better, and the stability of Serum A is also better.

5.0 Conclusion of Clinical Testing.

Based on the data it is generally seen that for all the under-eye attributes (dark circle, puffiness, fine lines, and wrinkles), good amount of improvement is seen after week-3 for Serum-A (N-[(2,4-Dihydroxyphenyl)ethylidene]glycine), compared to untreated area. These clinical tests further establish that both Serum A and B provide the treatments for the following group of skin conditions:

(i) Darkened skin including age spots, circles around eyes and stretch marks, (ii) Acne, (iii) Inflammation including intra-cellular and extra-cellular inflammation, (iv) Skin aging including wrinkles and fine lines, and (v) Loss of collagen including thinning skin and loss of skin pliability.

Antioxidant Testing Results.

Example 29

Antioxidant Testing of Serum A

Procedure. The liquid of Example 2, Serum A is stored at room temperature in a container. A lid is laid across the top of the container to slow evaporation. The lid does not prevent ambient air from slowly entering the container. After six months the liquid is still clear and colorless.

Example 30

Antioxidant Testing of Serum B

Procedure. The liquid of Example 2, Serum B is stored at room temperature in a container. A lid is laid across the top of the container to slow evaporation. The lid does not prevent ambient air from slowly entering the container. After six months the liquid is yellowish orange.

Example 31

Antioxidant Testing of Serum A

Procedure. The liquid of Example 2, Serum A is stored at 50 degrees Celsius in a container. A lid is laid across the top of the container. After four weeks the liquid is still clear and colorless.

Example 32

Antioxidant Testing of Serum B

Procedure. The liquid of Example 2, Serum B is stored at 50 degrees Celsius in a container. A lid is laid across the top of the container. After four weeks the liquid is brownish orange.

CONCLUSION OF ANTIOXIDANT TESTING

Composition of Serum A is more antioxidant than Serum B, while both of them have acceptable antioxidant efficacy.

The invention claimed is:

1. A method of treating a skin or a hair condition by topical application of a compound of formula (I) or a salt thereof;

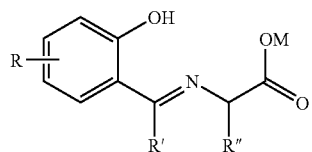

Compound of formula (I)

wherein:

R is selected from hydroxy, alkyl, substituted alkyl and halogen;

R' is selected from alkyl, substituted alkyl and heterocyclic;

R" is selected from alkyl substituted alkyl, aryl and heterocyclic;

M is selected from H, Li, Na, K, Ca, Mg, Zn, Mn, Cu, Fe, Co, Mo, V, Cr, ammonium, alkyl ammonium and nitrogen heterocyclic ammonium;

wherein said skin or hair condition is selected from a group consisting of acne, darkened skin, dark circles around the eyes, stretch marks, wrinkles and fine lines, loss of collagen, loss of skin pliability, hair graying and combinations thereof.

2. A method according to claim 1, wherein said skin or hair condition is selected from a group consisting of darkened skin, dark circles around the eyes and stretch marks.

3. A method according to claim 1, wherein said skin or hair condition is selected from a group consisting of wrinkles and fine lines.

4. A method according to claim 1, wherein said skin or hair condition is hair graying.

5. A method according to claim 1, wherein said skin or hair condition is selected from a group consisting of loss of collagen and skin pliability.

6. A method according to claim 1, wherein said skin or hair condition is acne.

* * * * *